United States Patent
Gerg et al.

(10) Patent No.: US 12,360,108 B2
(45) Date of Patent: Jul. 15, 2025

(54) BIOTIN-SPECIFIC MONOCLONAL ANTIBODY AND USE THEREOF

(71) Applicant: Roche Diagnostics Operations, Inc., Indianapolis, IN (US)

(72) Inventors: Michael Gerg, Munich (DE); Klaus Hirzel, Baierbrunn (DE); Caroline Hojer, Munich (DE); Erasmus Huber, Finning (DE); Hans-Peter Josel, Weilheim (DE); Thomas Meier, Munich (DE); Michael Schraeml, Penzberg (DE); Leopold Von Proff, Hohenpeissenberg (DE)

(73) Assignee: Roche Diagnostics Operations, Inc.

( * ) Notice: Subject to any disclaimer, the term of this patent is extended or adjusted under 35 U.S.C. 154(b) by 0 days.

(21) Appl. No.: 17/551,716

(22) Filed: Dec. 15, 2021

(65) Prior Publication Data

US 2022/0107309 A1 Apr. 7, 2022

Related U.S. Application Data

(60) Division of application No. 16/450,176, filed on Jun. 24, 2019, now abandoned, which is a continuation of application No. PCT/EP2017/083572, filed on Dec. 19, 2017.

(30) Foreign Application Priority Data

Dec. 27, 2016 (EP) .................................. 16206944
Jul. 31, 2017 (EP) .................................. 17184142

(51) Int. Cl.
*G01N 33/543* (2006.01)
*C07K 16/44* (2006.01)

(52) U.S. Cl.
CPC ....... *G01N 33/54306* (2013.01); *C07K 16/44* (2013.01)

(58) Field of Classification Search
CPC ...... C07D 495/04; C07K 16/00; C07K 16/40; C07K 16/44; C07K 2317/34; C07K 2317/92; G01N 33/54306
See application file for complete search history.

(56) References Cited

U.S. PATENT DOCUMENTS

| | | | |
|---|---|---|---|
| 4,816,566 A | 3/1989 | DeChiara et al. |
| 5,198,517 A | 3/1993 | Neilsen et al. |
| 5,198,537 A | 3/1993 | Huber et al. |
| 5,545,806 A | 8/1996 | Lonberg et al. |
| 5,545,807 A | 8/1996 | Sirani et al. |
| 5,569,825 A | 10/1996 | Lonberg et al. |
| 5,591,828 A | 1/1997 | Bosslet et al. |
| 5,625,126 A | 4/1997 | Lonberg et al. |
| 5,633,425 A | 5/1997 | Lonberg et al. |
| 5,661,016 A | 8/1997 | Lonberg et al. |
| 6,242,610 B1 | 6/2001 | Strongin et al. |
| 6,869,606 B1 | 3/2005 | Newman et al. |
| 9,765,153 B2 | 9/2017 | Brinkmann et al. |
| 2001/0016343 A1 | 8/2001 | Strongin et al. |
| 2004/0013844 A1 | 1/2004 | Mao |
| 2004/0138446 A1 | 7/2004 | Kharrat et al. |
| 2019/0309091 A1 | 10/2019 | Gerg et al. |
| 2019/0324024 A1 | 10/2019 | Gerg et al. |
| 2019/0324025 A1 | 10/2019 | Gerg et al. |
| 2021/0317232 A1 | 10/2021 | Jin |

FOREIGN PATENT DOCUMENTS

| | | |
|---|---|---|
| CA | 2412495 A1 | 12/2001 |
| CN | 103969438 A | 8/2014 |
| CN | 110088139 A | 8/2019 |
| DE | 3320140 A1 | 12/1984 |
| EP | 0371262 A1 | 6/1990 |
| EP | 0404097 A2 | 6/1990 |
| EP | 0747447 A2 | 6/1996 |
| JP | S5210288 A | 1/1977 |
| JP | 2008094721 A1 | 4/2008 |
| JP | 6024590 A | 11/2016 |
| WO | 8800593 A1 | 1/1988 |
| WO | 1991010741 A1 | 7/1991 |
| WO | 199301161 A1 | 1/1993 |
| WO | 1996033735 A1 | 10/1996 |
| WO | 1996034096 A1 | 10/1996 |
| WO | 1998024893 A3 | 6/1998 |

(Continued)

OTHER PUBLICATIONS

Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Dakshinamurti et al., "Production and characterization of a monoclonal antibody to biotin," Biochem J., 1986, vol. 237, No. 2, pp. 477-482.*
Li, Bai, Preparation of biotinylated anti-cytokine monoclonal antibodies, Immunolgoical Journal, No. 03, Mar. 25, 2001.
Wanshun, Liu et al,, Preparation and, Purification of Antibiotin Protein, Chinese Journal of Biochemical Pharmaceutics, No. 03, Sep. 30, 1984.

(Continued)

*Primary Examiner* — Galina M. Yakovleva

(57) ABSTRACT

The present invention relates to a monoclonal antibody capable of binding to biotin. In one embodiment the monoclonal antibody according to the invention also does not bind to a biotin moiety on a biotinylated molecule, wherein the biotin moiety is attached to the molecule via the carbon atom of the carboxyl function of the valeric acid moiety of biotin. Also disclosed is a method for generation of an antibody as discloed herein. The monoclonal antibody according to the invention is of specific use in a method for measuring an analyte in a sample, wherein a (strept)avidin/biotin pair is used to bind a biotinylated analyte specific binding agent to a (strept)avidin coated solid phase.

2 Claims, 7 Drawing Sheets

(56) References Cited

FOREIGN PATENT DOCUMENTS

| WO | 0050088 | A2 | 8/2000 |
|---|---|---|---|
| WO | 2001034651 | A1 | 5/2001 |
| WO | 0195857 | A2 | 12/2001 |
| WO | 0242311 | A2 | 5/2002 |
| WO | 2006050262 | A2 | 5/2006 |
| WO | 2014006123 | A1 | 1/2014 |
| WO | 2014039768 | A1 | 3/2014 |
| WO | 2015101586 | A1 | 7/2015 |
| WO | 2015165357 | A1 | 11/2015 |
| WO | 2016046574 | A1 | 3/2016 |
| WO | 2016065248 | A1 | 4/2016 |
| WO | 2018122205 | A2 | 7/2018 |
| WO | 2020028776 | A1 | 2/2020 |

OTHER PUBLICATIONS

Jakobovits, Aya et al., Analysis of homozygous mutant chimeric mice: Deletion of hte immunoglobulin heavy-chain joining region blocks B-cell development and antibody production, Proc. Natl. Acad. Sci. USA vol. 90, pp. 2551-2555, Mar. 1993.

Clackson et al., Making antibody fragments using phage display libraries, Letters to Nature, 1991, vol. 352, 5-pages pp. 624-628.

Ardes-Guisot et al., Selection of the biological activity of DNJ neoglycoconjugates through click length variation of the side chanin; Or. Biolmol. Chem., Aug. 7, 2011, vol. 9, No. 15, pp. 5373-5388.

Amspacher et al., Synthesis of a reaction intermediate analogue of biotin-dependent carboxylases via a selective derivatization of biotin; Org. Lett., Jul. 15, 1999, vol. 1, No. 1, pp. 99-102.

Bagci et al., Monoclonal Anti-Biotin Antibodies Simulate Avidin in the Recognition of Biotin; FEBS Letters, My, 1993, vol. 322, No. 1, pp. 47-50.

Brunner et al., Cell-Penetrating and Neurotargeting Dendritic siRNA Nanostructures; Angewandte Chemie; A Journal of the German Chemical Society; Feb. 2, 2015, vol. 54, No. 6, pp. 1946-1949.

Cao et al., Development of a bispecific monoclonal antibody as a universal immunoprobe for detecting biotinylated macromolecules; J. Immunol. Methods, Nov. 1, 1998, vol. 220, No. 1 & 2, pp. 85-91.

Chothia et al., Canonical structures for the hypervariable regions of immunoglobulins; J. Mol. Biol., Aug. 20, 1987, vol. 196, No. 4, pp. 901-917.

Clackson et al., Making antibody fragments using phage display libraries; Letter to Nature; Nature, Aug. 15, 1991, vol. 252, pp. 624-628.

Dakshinamuni et al., Production and characterization of a monoclonal antibody to biotin; Jul. 15, 1986, Biochemical Journal; vol. 237, No. 2, pp. 477-482.

Fang et al., Fluoride-cleavable biotinylation phosphoramidite for 5'-end-labeling and affinity purification of synthetic oligonucleotides; Nucleic Acids Research, Jan. 15, 2003, vol. 31, No. 2, pp. 708-715.

Fellouse et al., Synthetic antibodies from a four-amino-acid code: A dominant role for tyrosine in antigen recognition; PNAS, Aug. 24, 2008, vol. 101, No. 34, pp. 12467-12472.

Fishwild et al., High-avidity human IgGk monoclonal antibodies form a novel strain of minilocus transgenic mice; Nature Biotechnology, Jul. 1996, vol. 14, pp. 845-851.

Glasel J., A Nuclear Magnetic Resonance Investigation of Biotin. The Biotin Sulfonium Ion; Biochemistry, 1966, vol. 5 and 6, pp. 1851-1855.

Hamers-Casterman et al., Naturally occurring antibodies devoid of light chains; Letters to Nature; Nature, Jun. 3, 1993; vol. 363, pp. 446-448.Hamers-Casterman et al., Naturally occurring antibodies devoid of light chains; Letters to Nature; Nature, Jun. 3, 1993; vol. 363, pp. 446-448.

Holliger et al., "Diabodies": Small bivalent and bispecific antibody fragments (bacterial expression/phage display/dyad/surface plasmon resonance); Proc. Natl. Acad. Sci, Biophysics; Jul. 1993, vol. 90, pp. 6444-3448.

Hongo et al., Development and Characterization of Murine Monoclonal Antibodies to the Latency-Associated Peptide of Transforming Growth Factor ß1; Hybridoma; Mury Ann Liebert, Inc., 1995, Department of Bioanalytical Technology, Genentech, Inc.; vol. 14, No. 3, pp. 253-260.

Hudson et al., Engineered antibodies; Nature Medicine, Jan. 2003, vol. 9, No. 1, pp. 129-134.

Indyk et al., Biotin content of paediatric formulae, early lactation milk and seasonal bovine milk powders by biosensor immunoassay; International Dairy Journal; 2014, vol. 35, pp. 25-31.

Jakobovits et al., Analysis of homozygous mutant chimeric mice: Deletion of the immunoglobulin heavy-chain joining region blocks B-cell development and antibody production; Proc. Natl. Acad. Sci, Genetics; Mar. 1993, vol. 90, pp. 2551-2555.

Jakobovits et al., Germ-line transmission and expression of a human-derived yeast artificial chromosome; Cell Genesys, Inc., Letters To Nature; Nature, Mar. 18, 1993; vol. 362, pp. 254-258.

Jena Bioscience: Safety Data Sheet (according to Regulation (EC) No. 1907/2006); Biotin Protein Labeling Kit. pp. 1-6, Version: 0002, Last Update: Jul. 23, 2021. www.jenabioscience.com.

Jewett et al., Cu-free click cycloaddition reactions in chemical biology; Chem. Soc. Ref., Apr. 2010, vol. 39, No. 4, pp. 1272-1279.

Johnson, L.C., The Synthesis of New Biotin Derivatives and Their Bioactivity; The Department of Chemistry, Dec. 2002; pp. 1-68.

Johnson et al., The Kabat Database and a Bioinformatics Example; Methods in Molecular Biology, 2003, vol. 248, Antibody Engineering: Methods and Protocols; pp. 11-25; http://kabatdatabase.com; Human Press, Totowa, NJ.

Kohen et al., Preparation and Properties of Anti-Biotin Antibodies; Methods in Enzymology, vol. 279, No. 47, Anti-Biotin Antibodies; Biotin and Derivatives, pp. 451-463.

Kohler et al., Continuous cultures of fused cells secreting antibody of predefined specificity; Nature, vol. 256, Aug. 7, 1975, pp. 495-497.

Lee et al., Bivalent antibody phage display mimics natural immunoglobulin; Journal of Immunological Methods; 2004, vol. 284, pp. 119-132.

Lee et al., High-affinity Human Antibodies from Phage-displayed Synthetic Fab Libraries with a Single Framework Scaffold; J. Mol. Biol., 2004, vol. 340, pp. 1073-1093.

Lett et al., Pummerer Reaction of Biotin Sulfoxides: An Access to New Functionalized Biotin Derivatives; (Analyse Conformationnelle De Derives DU Thiophane, Des Sulfoxydes ET Sulfones Correspondants); Tetrahedron; 1974, vol. 30, pp. 3365-3377, English Abstract.

Lett et al., Pummerer Reaction of biotin sulfoxides: an access to new functionalized biotin derivatives; Tetrahedron Letters, 1982, vol. 23, No. 52, pp. 5541-5544.

Lloyd et al., Modelling the human immune response: performance of a 1011 human antibody repertoire against a broad panel of therapeutically relevant antigens; Protein Engineering, Design and Selection, Mar. 2009, vol. 22, No. 3, pp. 159-168.

Longberg et al., Letters to Nature; Antigen-specific humanantibodies from mice comprising four distinct genetic modifications; Nature, Apr. 28, 1994, pp. 856-859.

Longberg et al., Human Antibodies from Transgenic Mice; Intern. Rev. Immunol., 1995, vol. 13, pp. 65-93.

Marks et al., By-Passing Immunization Human Antibodies from V-gene Libraries Displayed on Phage; J. Mol. Biol., 1991, vol. 222, pp. 581-597.

Marks et al., By-Passing Immunization: Building High Affinity Human Antibodies By Chain Shuffling; 1992 Nature Publishing Group; http://www.nature.com/naturebiotechnology; Biotechnology, Jul. 1992, vol. 10, pp. 779-783.

Marquet, A., New Aspects of the Chemistry of Biotin and of some Analogs; Pure & Appl. Chem., Pergamon Press, 1977, vol. 49, pp. 183-196.

Melville et al., The Structure of Biotin: the Formation Of Thiophenevaleric Acid From Biotin; The Department of Biochemistry, Cornell University Medical College, New York City; Sep. 25, 1942; vol. 146, pp. 487-492.

(56) References Cited

OTHER PUBLICATIONS

Morrison, S.L., Chimeric human antibody molecules: Mouse antigen-binding domains with human constant region domains; Proc. Natl. Acad. Sci; Nov. 1984, vol. 81, pp. 6851-3855, Immunology.

Morrison, S.L., Success in Specification; Immunology, Nature, Apr. 28, 1994, vol. 368, pp. 812-813.

Neuberger, M., Generating high-avidity human Mabs in mice; 1996, Nature Biotechnology, vol. 14, p. 826.

Ohrui et al., Stereopecific Synthesis of (+)-Biotin; Tetrahedron Letters No. 32, 1975, pp. 2765-2766.

Preston, P.N., The Chemistry of Heterocyclic Compounds; Condensed Imidazoles, 5-5 Ring systems; 1986, pp. 196-199, John Wiley & Sons, Inc.

Rodriguez-Melendez et al., Diaminobiotin and Desthiobiotin Have Biotin-Like Activities in Jurkat Cells; Nutrient-Gene Interactions; Jan. 16, 2003; vol. 133, No. 5, pp. 1259-1264.

Seeber et al., A Robust High Throughput Platform to Generate Functional Recombinant Monoclonal Antibodies Using Rabbit B Cells from Peripheral Blood; PLOS ONE; www.plosone.org; Feb. 2014, vol. 9, No. 2, pp. e86184.

Sheriff et al., Redefining the minimal antigen-binding fragment; Nature Publishing Group; Nature Structural Biology; 1996, vol. 3, No. 9, pp. 733-736.

Sidhu et al., Phage-displayed Antibody Libraries of Synthetic Heavy Chain Complementarity Determining Regions; J. Mol. Biol., 2004, vol. 338, pp. 299-310.

Slavoff et al., Expanding the Substrate Tolerance of Biotin Ligase through Exploration of Enzymes from Diverse Species; J. Am. Chem. Soc., (JACS Communications), Jan. 3, 2008; vol. 130, pp. 1160-1162.

Sundburg et al., Spatially-Addressable Immobilization of Macromolecules on Solid Supports; J. Am. Chem. Soc., 1995, vol. 117, pp. 12050-12057.

Wu et al., Matrix interference in serum total thyroxin (T4) time-resolved fluorescence immunoassay (TRFIA) and its elimination with the use of streptavidin-biotin separation technique; Clinica Chimica Acta; 2001, vol. 308, pp. 117-126.

Yi et al., Sulfonium alkylation followed by 'click' chemistry for facile surface modification of proteins and tobacco mosaic virus; Tetrahedron Letters; 2009, vol. 50, pp. 759-762.

Report on Advances in Immunology, vol. 2014-2015; Research progress and development trend of antibodies and antibody engineering; Apr. 30, 2016, pp. 220-221. English Translation provided.

Huston et al., Protein Engineering of Single-Chain Fv Analogs and Fusion Proteins; Antibodies and Antigens; Methods in Enzymology, vol. 203, 1991, Biosynthetic Antibody Binding Site Proteins; pp. 46-88.

Xu et al., Diversity in the CDR3 Region of VH Is Sufficient for Most Antibody Specificities; Cell Press; Immunity, Jul. 2000, vol. 13, pp. 37-45.

Lonberg, Nils et al., Antigen-specific human antibodies from mice comprising four distinct genetic modifications, Nature, 1994, pp. 856-859, vol. 368.

Marks, James D. et al., By-passing Immunization Human Antibodies from V-gene Libraries Displayed on Phage, Journal of Molecular Biology, 1991, pp. 581-597, vol. 222.

* cited by examiner

D(+)-Biotin

BIOTIN-SPECIFIC MONOCLONAL ANTIBODY AND USE THEREOF

CROSS-REFERENCE TO RELATED APPLICATIONS

This application is a U.S. Divisional Application of U.S. application Ser. No. 16/450,176 filed Jun. 24, 2019, which is a continuation of International Application No. PCT/EP2017/083572 filed Dec. 19, 2017, which claims priority to European Application No. 16206944.7 filed Dec. 27, 2016, and European Application No. 17184142.2 filed Jul. 31, 2017, the disclosures of which are hereby incorporated by reference in their entirety.

BACKGROUND OF THE INVENTION

The present invention relates to a monoclonal antibody capable of binding to biotin. In one embodiment the monoclonal antibody according to the invention also does not bind to a biotin moiety on a biotinylated molecule, wherein the biotin moiety is attached to the molecule via the carbon atom of the carboxyl function of the valeric acid moiety of biotin. Also disclosed is a method for generation of an antibody as disclosed herein. The monoclonal antibody according to the invention is of specific use in a method for measuring an analyte in a sample, wherein a (strept)avidin/biotin pair is used to bind a biotinylated analyte specific binding agent to a (strept)avidin coated solid phase.

In living organisms as well as in biochemistry in vitro, the primary function of biotin is that of a co-substrate which is required as a prosthetic group for enzymes with carboxytransferase activity, e.g. pyruvate carboxylase and acetyl-CoA-carboxylase. In bacteria, biotin is attached to biotin carboxyl carrier protein by biotin protein ligase. Further, a number of chemical processes are known with which biotin can be covalently attached to a suitable group on almost any molecule of interest. As a common feature, the carbon atom of the carboxyl function of the valeric acid side chain is reacted in a coupling reaction to an appropriate (receiving) group on the molecule of interest, or to a reactive group of a linker, wherein the linker itself is either already connected to the molecule of interest or the linker is coupled to the molecule once biotin is attached to the linker. Generally, such attachment of biotin to various chemical sites via the carbon atom of the carboxyl function of the valeric acid side chain is referred to as biotinylation.

The extraordinary affinity of avidin and/or streptavidin (=(strept)avidin), respectively, for biotin ($K_a = 10^{15}$ $M^{-1}$) is one of the strongest known non-covalent interactions of a protein and a ligand. It allows biotinylated molecules in a complex mixture to be specifically bound by (strept)avidin. For this reason avidin and/or streptavidin are used in a large number of immunological detection assays.

Besides a strong affinity for (strept)avidin, two further properties make biotin particularly suited for tagging proteins and other macromolecules. Firstly, the biotin molecule is substantially smaller than proteins. Its molecular size allows one or more biotin molecules to be conjugated to a molecule of interest while minimizing loss of biological function of such molecule. Secondly, the terminal carbon atom of the valeric acid side chain of biotin can be derivatized easily, thereby facilitating conjugation to reactive moieties on a molecule of interest, particularly a protein. Notably biotinylation does no change the structure of the heterocyclic moiety of biotin.

After biotinylation via the terminal carbon atom of the valeric acid side chain the biotin moiety preserves the capability to interact specifically with (strept)avidin, as the moiety of the biotin molecule that is responsible for specific interaction with the binding pocket of avidin-type proteins is the heterocyclic structure represented by the ureido ring that is fused with the tetrahydrothiophene ring is not affected.

The heterocyclic structure of biotin is also targeted by monoclonal antibodies (mAbs) of the prior art against biotin. Kohen F. et al. (Methods in Enzymology 279 (1997) 451-463) generated monoclonal antibodies using as an immunogen biotinylated bovine serum albumin (BSA conjugated with N-hydroxysuccinimidobiotin). The document reports analysis of amino acid sequences of antigen binding regions of antibodies capable of binding the biotin moiety of a biotinylated protein. Sequence alignments were made with homologous stretches of the polypeptide sequences of avidin and streptavidin which were reported to interact with the bicyclic ring system of biotin. Notably, similarities with the polypeptide sequences of avidin and streptavidin were identified in the CDR2 and CDR3 of biotin-specific antibodies. The results were interpreted in that in the amino acid sequences of biotin binding pockets a common pattern is necessary for biotin binding.

Dakshinamurti, K et al. (Biochem. J. 237 (1986) 477-482) report the generation and characterization of murine mAbs using as an immunogen keyhole limpet hemocyanin (KLH) to which an activated form of biotin (N-hydroxysuccinimidobiotin) was coupled. Several hybridoma clones were obtained, and the respective mAbs were effective in binding free biotin, hapten-conjugated biotin, protein-conjugated biotin, and biocytin. Notably, biocytin is a naturally occurring derivative of biotin, an amide formed from the valeric acid carboxyl function and the amino acid L-lysine. The fact that such derivatized biotin is bound by the mAbs of Dakshinamurti, K et al. (supra) indicates a binding specificity which targets the heterocyclic structure of biotin, i.e. the ureido ring that is fused with the tetrahydrothiophene ring.

While the mAbs reported by Dakshinamurti, K et al. (supra) do bind conjugated biotin and also free biotin, JP 2008-094721 discloses a mAb that specifically binds to protein-conjugated biotin, but not to free biotin. Table 1 summarizes the discussed properties of the prior art antibodies.

TABLE 1

Binding properties of monoclonal antibodies raised against biotin

| Report | binding to biotinylated target | binding to free biotin |
|---|---|---|
| Dakshinamurti, K et al. (Biochem. J. 237 (1986) 477-482) | yes | yes |
| Kohen F. et al. (M. Enzymol. 279 (1997) 451-463) | yes | not determined |
| JP 2008-094721 | yes | no |
| no report, yet | no | yes |

Similar to the report of Dakshinamurti, K et al. (supra), WO 00/50088 A2 deals with antibodies useful for therapeutic intervention; specifically, antibodies are reported here which have an affinity for conjugated biotin one to four orders of magnitude greater than the respective affinity for free biotin. The document discloses immunization with an antigen to which biotin is conjugated via the carbon atom of the carboxyl function of the valeric acid moiety. In a first screening step antibodies are identified which bind to the conjugated biotin; a subsequent second screening step is disclosed which aims at identifying clones secreting monoclonal antibodies capable of binding to the conjugated biotin even in the presence of a defined amount of free biotin. Notably, the document is silent concerning monoclonal antibodies which on the one hand bind to free biotin (biotin that is not covalently bound to another molecule and which is in dissociated form in aqueous solution) but on the other hand do not bind to the biotin moiety on a biotinylated molecule, i.e. a biotin moiety which could also be bound by (strept)avidin.

Indyk H. E. et al. International Dairy Journal 35 (2014) 25-31 report an optical biosensor assay for the detection of free biotin in milk. A Biacore Q biosensor with a CM5 sensor chip was used; on an amine-modified sensor surface biotin was immobilized by covalent coupling of its NHS-activated valeric acid terminal carboxylate group. Notably, the orientation of the biotin molecules coupled to the sensor chip was the same as for biotin on biotinylated molecules, i.e. corresponds to a biotin moiety which could also be bound by (strept)avidin. Thus, primarily the heterocyclic structure of biotin was exposed for antibody binding. Binding properties of three different biotin-specific polyclonal antibodies and two different monoclonal antibodies were characterized using the biotin sensor chip, in the presence of different concentrations of free biotin as competitor.

Notably, no disclosure has been found in the prior art, so far, that describes a monoclonal antibody which specifically binds to free biotin, but not to the conjugated biotin on a biotinylated target molecule. Such an antibody would bind the biotin primarily from its "tail", i.e. would importantly interact with the valeric acid moiety of biotin. In particular, no antibody has been described, so far, which on the one hand specifically binds to free biotin, but on the other hand does not bind to conjugated biotin, wherein conjugated biotin is attached to the target molecule via the carbon atom of the carboxyl function of the valeric acid moiety, whereby the heterocyclic "head" structure of biotin is located distal from the target molecule. Further, no monoclonal antibody is known, so far, which in aqueous solution is characterized by an affinity for free biotin $K_s$[free] that is higher than the affinity of the same monoclonal antibody for conjugated biotin $K_s$[conj.], wherein the conjugated biotin is conjugated via the carbon atom of the carboxyl function of the valeric acid moiety (see above), and wherein $K_s$[free] differs from $K_s$[conj.] by a factor of at least 50, 100, 500, 1,000, 5,000, 10,000, 50,000, or at least 100,000.

Johnson L. C. ("The synthesis of new biotin derivatives and their bioactivity", Master of Science thesis dated December 2002, submitted to the Graduate Faculty of the Louisiana State University and Agricultural and Mechanical College (US) retrieved from the internet on Feb. 16, 2017; URL: http://etd.lsu.edu/docs/available/etd-0927102-135929/unrestricted/Johnson_thesis.pdf) describes chemical reactions of derivatization of the heterocyclic "head" structure of biotin. Embodiments are disclosed wherein the 1'-N atom comprised in the heterocyclic structure of biotin is targeted by derivatization.

Wu F.-B. et al. Clinica Chimica Acta 308 (2001) 117-126 disclose a method to counteract matrix interference in a competitive immunoassay. An initial assay setup consisting of an immobilized second antibody bound to a target (serum thyroxin) specific antibody was replaced. The replacement was provided by firstly immobilizing biotinylated bovine serum albumin (BSA), followed by binding streptavidin to the biotinylated BSA, followed by binding the target-specific antibody to the streptavidin, wherein prior to this step the target-specific antibody was biotinylated. It was found that such a setup provided increased binding capacity for the target of the assay (serum thyroxin) and thereby increased resistance to matrix interference.

The present invention provides chemical structures of Formula I (see below) which specifically present the valeric acid "tail" moiety of a derivatized biotin as the distal (most terminal) part of the respective structure. By way of derivatizing biotin and attaching its "head" moiety to the rest of the structure of Formula I, the valeric acid moiety is primarily exposed and presented for physical interaction, including interaction with immune cell receptors and antibodies. It was hypothesized that an antibody interacting with the derivatized biotin according to Formula I would have binding properties that could target the valeric acid "tail" moiety. In the present study it was further tested whether the monoclonal antibodies that can be elicited using a structure of Formula I, and which are capable of reacting with such a structure would also have the properties of a desired antibody according to the invention.

Accordingly, a desired antibody of the invention is a monoclonal antibody which specifically binds biotin, wherein the biotin is not covalently bound to another molecule. Also in line with the above reasoning, a desired antibody of the invention is a monoclonal antibody which specifically binds biotin, wherein the biotin is in dissociated form in aqueous solution. At the same time, a desired antibody of the invention does not bind to conjugated biotin on a biotinylated target molecule, wherein the biotin is attached to the target molecule via the carboxy group of the valeric acid moiety. In such a biotinylated target molecule, the conjugated form of the "head" structure of the biotin is presented and can be bound, e.g. by a (strept)avidin.

Thus the inventors set out to find out whether antibodies could be made and isolated to specifically bind free biotin. Such binding to biotin would have a completely different structural basis compared to the already described antibodies of earlier reports which bind to the "head" portion of biotin.

Thus, it was an objective of the present invention to provide a monoclonal antibody specifically binding the compound of Formula I

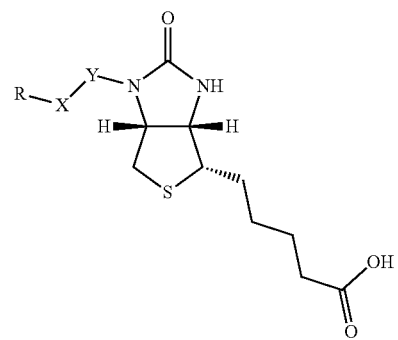

(Formula I)

characterized in that it also binds to biotin, wherein Y is $CH_2$ or $C=O$, X is O or $(CH_2)_n$ and n is an integer from 1 to 20, and R is either H, or Z-L, wherein L is a linker, and Z is selected from a hapten not containing a biotin moiety and a polypeptide.

It was a further objective to provide a monoclonal antibody binding to a molecule of Formula I and to biotin but not to conjugated biotin which is attached to a macromolecule via the carbon atom of the carboxyl function of the valeric acid moiety. As a further objective the antibody of the present invention is binding to biotin comprising a chemically unmodified valeric acid moiety. It was hence an objective to isolate a monoclonal antibody with an affinity for conjugated biotin on a biotinylated target molecule which is lower than the affinity for free biotin by a factor selected from the group consisting of at least 50, 100, 500, 1,000, 5,000, 10,000, or higher. In other words, an objective was to isolate a monoclonal antibody with an affinity for free biotin which is higher than the affinity for conjugated biotin on a biotinylated target molecule by a factor selected from the group consisting of at least 50, 100, 500, 1,000, 5,000, and at least 10,000.

It has now surprisingly been found that such a monoclonal antibody can be generated and isolated.

Recently, high dosage biotin supplementation has become "fashionable". Biotin is believed to be a key contributor to keratin, and high dose biotin thus could improve quality and quantity of hair, nails and skin. Biotin is water-soluble and excreted rapidly. However, if high dose biotin supplementation is taken, rather high levels of biotin in the circulation may be present and the biotin in the circulation will also be present in a sample used for in vitro analysis for measurement of an analyte, i.e. in a sample like serum or plasma. Biotin comprised in a sample, if present at high levels might interfere in an assay for measurement of an analyte, which is employing a (strept)avidin coated solid phase and a biotinylated specific binding agent.

Therefore, with the increased use of high dose biotin supplements, an increasing need exists to reduce the potential interference by abnormally high biotin levels in a sample with the measurement of an analyte from the same sample in assays which are based on the (strept)avidin-biotin binding pair.

It was a further task to investigate whether the antibodies as disclosed herein can be used to reduce the potential interference of biotin. It has been surprisingly found that a monoclonal antibody capable of binding biotin but not binding the biotin moiety on a biotinylated target molecule is particularly useful to counteract a potential interference caused by abnormally high levels of biotin in a sample in a method for measuring an analyte in such sample, in an assay wherein a (strept)avidin/biotin pair is used to bind a biotinylated analyte specific binding agent to a (strept)avidin coated solid phase.

SUMMARY OF THE INVENTION

Herein is reported a monoclonal antibody specifically binding the compound of Formula I,

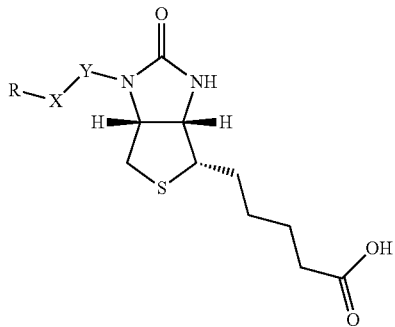

(Formula I)

characterized in that it also binds to biotin, wherein Y is $CH_2$ or C—O, X is O or $(CH_2)_n$ and n is an integer from 1 to 20, and R is either H, or Z-L, wherein L is a linker, and Z is selected from a hapten not containing a biotin moiety and a polypeptide.

Further reported is a method for measuring an analyte in a sample, wherein a (strept)avidin/biotin binding pair is used to bind a biotinylated analyte specific binding agent to a (strept)avidin coated solid phase, the method comprising adding to the sample (a) an antibody as reported herein, (b) a biotinylated analyte specific binding agent, (c) a streptavidin coated solid phase, followed by measuring the analyte bound to the solid phase via (strept)avidin and biotinylated analyte specific binding agent.

Further reported is a method for measuring an analyte in a sample, wherein a (strept)avidin/biotin binding pair is used to bind a biotinylated analyte specific binding agent to a label, the method comprising adding to the sample (a) an antibody as reported herein, (b) a biotinylated analyte specific binding agent, (c) a (strept)avidin bound to a label, followed by separating the complex comprising the analyte, the biotinylated analyte specific binding agent and the labeled streptavidin, and determining the amount of label bound to the analyte.

Further reported is the use of an antibody as reported herein, in a method for measuring an analyte in a sample, wherein a (strept)avidin/biotin pair is used to bind a biotinylated analyte specific binding agent to a (strept)avidin coated solid phase or to a labeled (strept)avidin.

Further reported is an immunoassay test kit comprising at least (a) an antibody as disclosed herein, (b) a biotinylated analyte specific binding agent, and (c) a (strept)avidin coated solid phase.

Further reported is an immunogen according to of Formula I

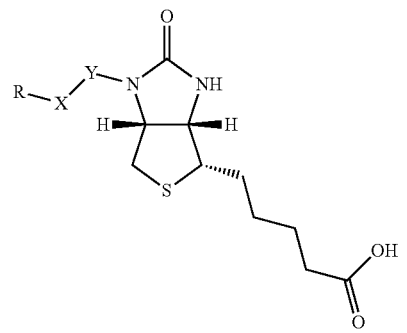

(Formula I)

wherein Y is $CH_2$ or C—O, X is O or $(CH_2)_n$ and n is an integer from 1 to 20, and R is Z-L, wherein L is a linker, and Z is a polypeptide of at least 30 amino acids, and preferably is keyhole limpet hemocyanin.

Further reported is a method for producing an antibody as disclosed herein, the method comprising the steps of (a) immunizing an experimental animal with an immunogen as disclosed herein, thereby inducing B-cells producing antibodies binding to the immunogen, (b) obtaining a monoclonal antibody binding to the immunogen produced by the B-cell of step (a), either via hybridoma technology or by B-cell PCR technology, (c) further selecting the antibody of step (b) for binding to biotin, thereby obtaining an antibody as disclosed herein.

A method for producing an antibody as disclosed herein, the method comprising the steps of a) immunizing an experimental animal with an immunogen as disclosed herein, thereby inducing B-cells producing antibodies binding to the immunogen, b) obtaining a monoclonal antibody binding to the immunogen produced by the B-cell of step (a), either via hybridoma technology or by B-cell PCR technology, c) selecting the antibody of step (b) for binding to biotin, and d) selecting those antibodies which do not bind to the compound of Formula II,

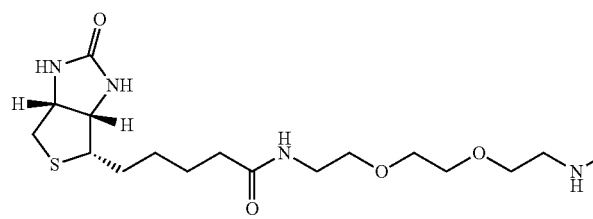

(Formula II)

thereby obtaining an antibody as disclosed herein.

DETAILED DESCRIPTION OF THE INVENTION

In one embodiment the present invention relates to a monoclonal antibody specifically binding the compound of Formula I,

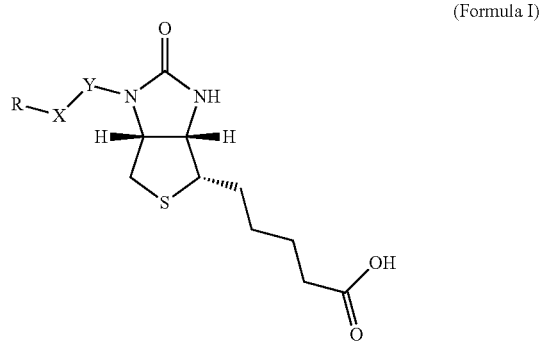

(Formula I)

characterized in that it also binds to biotin,
wherein
Y is $CH_2$ or C—O,
X is O or $(CH_2)_n$, and n is an integer from 1 to 20, and
R is either H, or Z-L,
wherein
L is a linker, and Z is selected from a hapten not containing a biotin moiety and a polypeptide.

Surprisingly it has been found that a monoclonal antibody binding to both, the structure of Formula I (which is described in more detail further below) and biotin can be reliably generated based on the methods disclosed herein which also are illustrated in more detail further below.

For the purpose of the present disclosure, in all aspects and embodiments mentioned herein, the term "(strept)avidin" and avidin-type protein can be used interchangeably. An avidin-type protein is generally understood as a protein with at least one binding pocket capable of binding specifically to the heterocyclic structure of biotin that is represented by the ureido ring that is fused with the tetrahydrothiophene ring. By virtue of this property, an avidin-type protein is capable of binding to a biotinylated target molecule, wherein biotin is covalently bound to the molecule via the carbon atom of the carboxyl function of the valeric acid side chain of biotin. Several embodiments of avidin-type proteins are known to the art. More specifically, an avidin-type protein can be selected from the group including avidin, neutravidin, streptavidin, bradavidin, traptavidin, a biotin-binding variant thereof, a mixture thereof, a monomer, dimer, trimer, tetramer or multimer thereof, a conjugated form thereof and an antibody binding to a conventionally biotinylated molecule of interest. It is known that in their naturally occurring forms a number of avidin-type proteins (especially those which are not antibodies), specifically avidin and streptavidin, are homotetramers; i.e. they consist of four identical subunits. In an embodiment of a variant of a monomeric avidin-type protein, the naturally occurring form may be a di-tri-, or tetra-oligomer with each monomer having a biotin binding pocket. In an embodiment the avidin-type protein is selected from a monomer, a homodimer, a homotrimer, and a homotetramer.

Figure 3A:
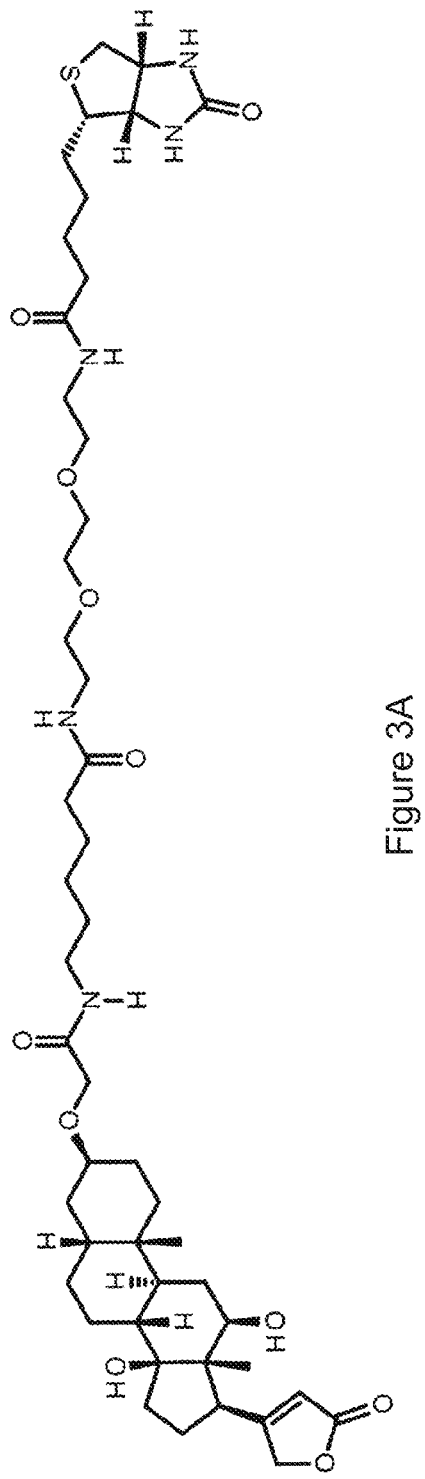

Also more specifically, an avidin-type protein can be an antibody with an antigen binding pocket capable of binding specifically to the heterocyclic structure of biotin that is represented by the ureido ring that is fused with the tetrahydrothiophene ring. Examples of antibodies with this property are known in the prior art and cited above. In an even more specific embodiment, an avidin-type protein can be identified if it specifically binds to the biotin moiety of the structure in FIG. 3A. In an even more specific embodiment, the avidin-type protein does not specifically bind to the structure in FIG. 3 B.

In one embodiment the (strept)avidin according to the present disclosure is selected from the group including avidin, neutravidin, streptavidin, bradavidin, traptavidin, a biotin-binding variant thereof, and a mixture thereof.

When referring to "(strept)avidin" or an avidin-type protein in the present disclosure, it is understood that these terms equally incorporate any variant thereof with the proviso that the variant is capable of binding biotin non-covalently with at least one binding pocket capable of binding specifically to the heterocyclic structure of biotin that is represented by the ureido ring that is fused with the tetrahydrothiophene ring. In this respect, a variant is a "functionally equivalent polypetide" in that the amino acids forming the at least one binding pocket bear similar electrostatic and sterochemical attributes of the amino acid sequence of the original avidin-type protein under consideration, wherein the variant comprises one or more conservative amino acid substitutions, analog amino acids substitutions and/or deletions and/or additions of amino acids that do not significantly affect or alter the function of the amino acids of the binding pocket. "Functionally equivalent" also includes a homologous amino acid sequence with regards to the respective referenced amino acid sequence. "Conservative substitutions" applies to both amino acid and nucleic acid sequences. With respect to particular nucleic acid sequences, "conservatively substituted" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions in a peptide, polypeptide, or protein sequence which alter a single amino acid or a small percentage of amino acids in the amino acid sequence is a "conservative substitution" where the alteration results in the substitution of an amino acid with a chemically similar amino acid. Conservative substitution tables providing functionally similar amino acids are known to those of ordinary skill in the art. Conservative substitution tables providing functionally similar amino acids are known to those of ordinary skill in the art. The following eight groups each contain amino acids that are conservative substitutions for one another:

The term "conservative amino acid substitutions" refers to all substitutions wherein the substituted amino acid has similar structural or chemical properties with the corresponding amino acid in the reference sequence. By way of example, conservative amino acid substitutions involve substitution of one aliphatic or hydrophobic amino acids, e.g., alanine, valine, leucine, isoleucine, methionine, phenylalanine, or tryptophan with another; substitution of one hydroxyl-containing amino acid, e.g., serine and threonine, with another; substitution of one acidic residue, e.g., glutamic acid or aspartic acid, with another; replacement of one amide-containing residue, e.g., asparagine and glutamine, with another; replacement of one aromatic residue, e.g., phenylalanine and tyrosine, with another; replacement of one basic residue, e.g., lysine, arginine and histidine, with another; and replacement of one small amino acid, e.g., alanine, serine, threonine, and glycine, with another.

As used herein "deletions" and "additions" in reference to amino acid sequence, means deletion or addition of one or more amino acids to the amino terminus, the carboxy-terminus, the interior of the amino acid sequence or a combination thereof, for example the addition can be to one of the antibodies subject of the present application.

As used herein, "homologous sequences" have amino acid sequences which are at least 70%, at least 80%, at least 90%, at least 95%, or at least 99% homologous to the corresponding reference sequences. Sequences which are at least 90% identical have no more than 1 alteration, i.e., any combination of deletions, additions or substitutions, per 10 amino acids of the reference sequence. Percent homology is determined by comparing the amino acid sequence of the variant with the reference sequence using, for example, MEGALIGN™ project in the DNA STAR™ program.

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

For the purpose of the present disclosure it is understood that the terms "biotin" or "free biotin" are used interchangeably and denote the naturally occurring compound, i.e. D(+)-biotin.

Figure 1A:
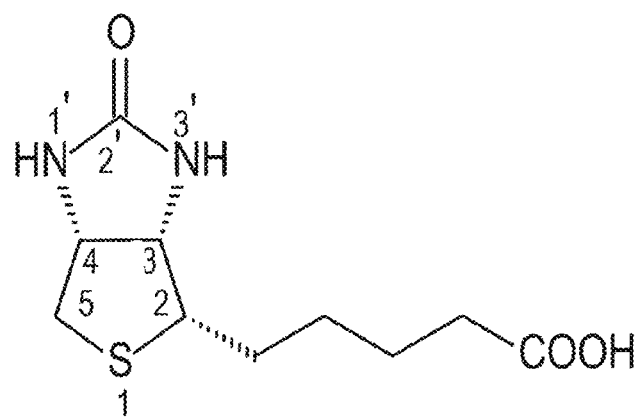
FIG. 1A D(+)-biotin
FIG. 1B D(+)-biotin
FIG. 2A Synthesis scheme of Example 1
FIG. 2B Synthesis scheme of Example 2
FIG. 3A Compound of Formula II
FIG. 3B Compound of Formula III
FIGS. 4A-4C Exemplary kinetic signatures from the antibody kinetic screening assay. Dotted line: SPR binding signal of the Dig-Biotin-conjugate-M-19.11-Fab' complex injection. Solid line: SPR binding signal of the Dig-Biotin-conjugate-M-19.11-Fab' complex supplemented with 300 nM d-biotin. Typically, three classes of free d-biotin blocking kinetics were observed.

Biotin (D(+)-biotin; $C_{10}H_{16}N_2O_3S$; MW=244.31 g/mol; IUPAC name: 5-[(3aS,4S,6aR)-2-oxo-1,3,3a,4,6,6a-hexahydrothieno[3,4-d]imidazol-4-yl] pentanoic acid), CAS Registry Number 58-85-5 comprises a ureido ring fused with a tetrahydrothiophene ring, and a valeric acid substituent which is attached to one of the carbon atoms of the tetrahydrothiophene ring. The basic structure of biotin is known since long and was reported e.g. by Melville D. B. et al. (J. Biol. Chem. 146 (1942) 487-492). Biotin has three contiguous chiral carbon atoms and therefore, four diastereomeric racemic forms are possible. Of the diastereomeric racemic forms, only D(+)-biotin occurs in nature whereas other isomers are of synthetic origin. The biologically active form is the (3aS,4S,6aR) configuration shown in FIG. 1A and FIG. 1B.

Figure 1B:
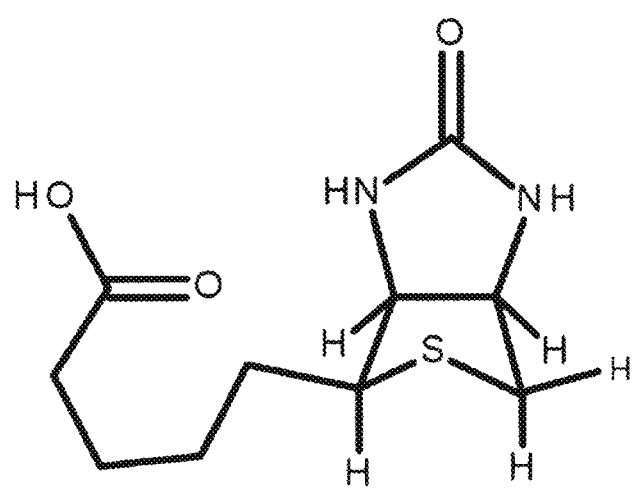
Figure 2A:
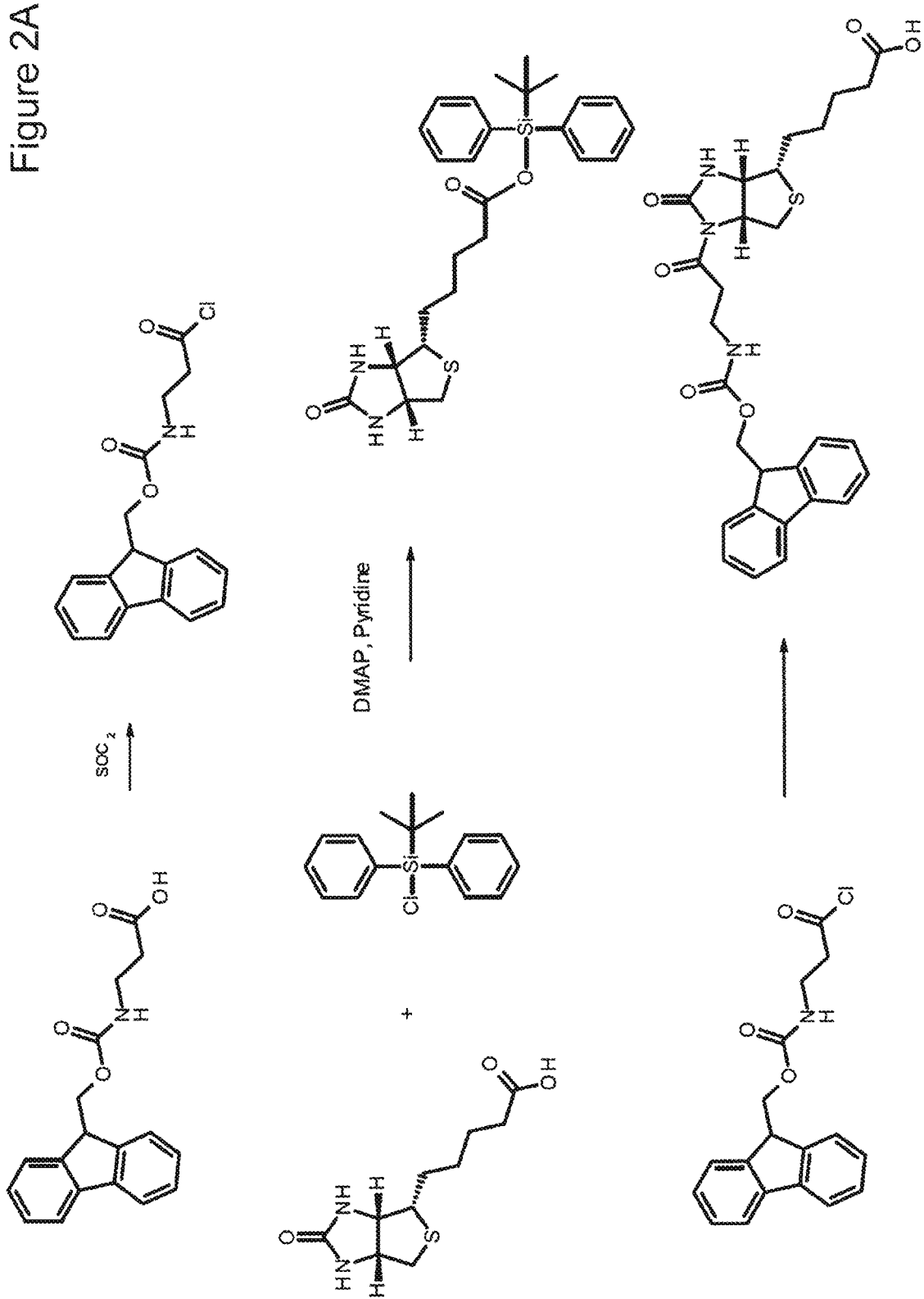
Figure 2B:
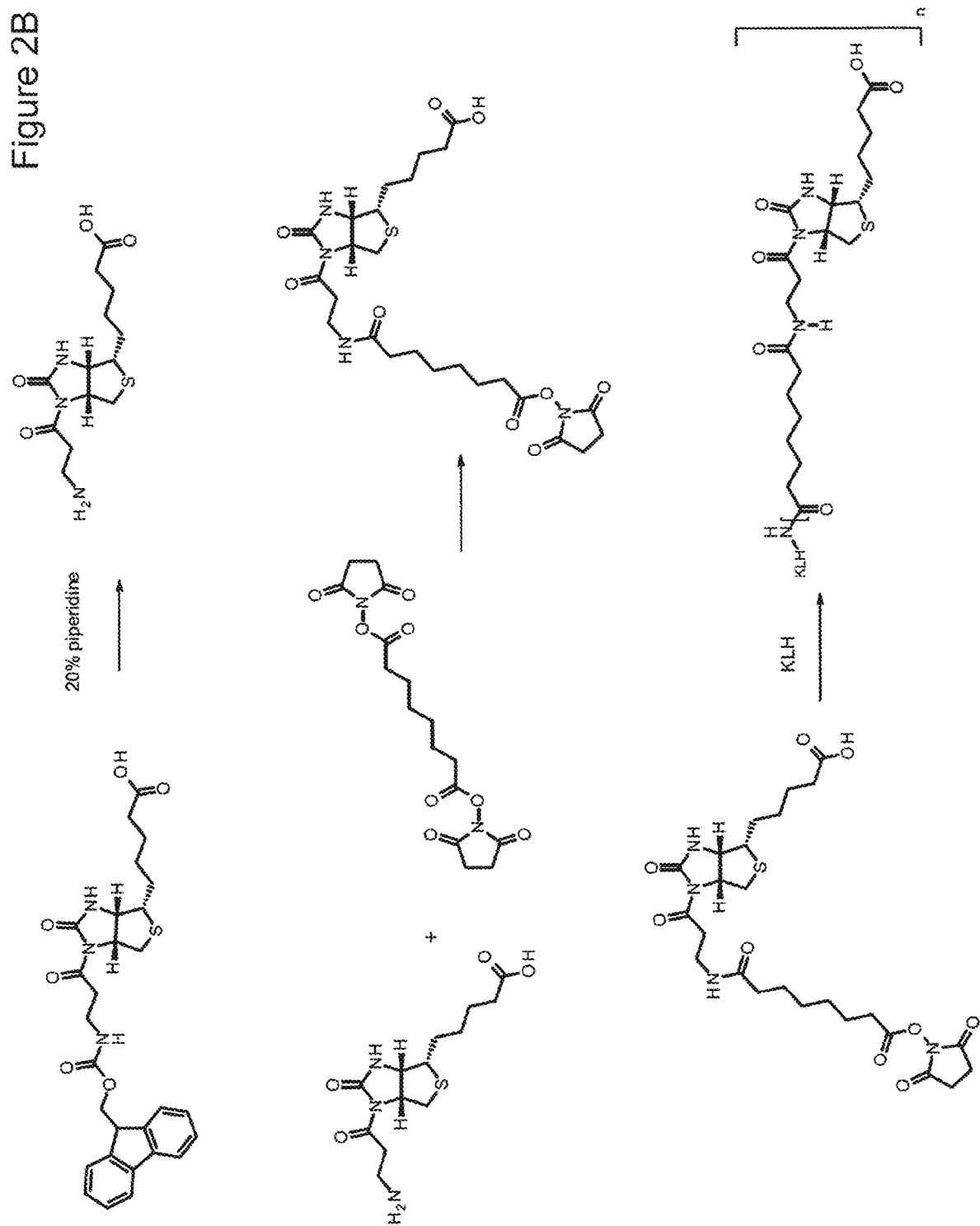

According to Marquet A. (Pure & Appl. Chem. 49 (1977) 183-196), in the crystal structure of D(+)-biotin the ureido ring is planar while the thiophane ring has an envelope conformation, as shown in FIG. 1B. The valeric acid side chain is not fully extended but twisted, and there is interaction between $C_6$ atom of the side chain and N'3 atom of the ureido ring; reportedly this interaction has an impact on the reactivity of biotin. The envelope conformation of the thiophane ring was also reported in solution, as shown by NMR studies reported by Glasel J. A. (Biochemistry 5 (1966) 1851-1855) and by Lett R. & Marquet A./Tetrahedron 30 (1974) 3365-3377).

The term "biotin moiety" is used to refer to the biotin-related part or biotin-derived part of a molecule as e.g. obtained by any kind of biotinylation or chemical coupling.

The attachment of biotin to an appropriate chemical group on a molecule of interest via the carbon atom of the carboxyl function of the valeric acid side chain is referred to as "biotinylation" or "conventional biotinylation". Accordingly, the biotin residue of a "biotinylated" molecule of interest has an outward-facing ring structure (i.e. the ureido ring that is fused with a tetrahydrothiophene ring), whereas the linear portion of the biotin residue is inward-facing, towards the surface of the biotinylated molecule. The outward-facing ring structure can be bound by an avidin-type protein. Thus, importantly the heterocyclic "head" structure of biotin needs to be exposed for specific binding by an avidin-type protein.

The term "(strept)avidin/biotin binding pair" is perfectly known to the person skilled in the art. It points to the fact that biotin (including the biotin moiety of a biotinylated molecule) on the one hand and (strept)avidin on the other hand represent the two members of this binding pair. As described above, this binding pair is outstanding in having one of the highest binding affinities known for non-covalent interactions.

The articles "a" and "an" are used herein to refer to one or to more than one (i.e., to at least one) of the grammatical object of the article. By way of example, "an antibody" means one antibody or more than one antibody.

The term "antibody" encompasses the various forms of antibody structures including, but not being limited to, whole antibodies and antibody fragments. The antibody according to the invention is preferably a goat, sheep, mouse, rabbit, or rat antibody, a chimeric antibody, or further genetically engineered antibody as long as the characteristic properties according to the invention are retained.

"Antibody fragments" comprise a portion of a full length antibody, preferably the variable domain thereof, or at least the antigen binding site thereof. Examples of antibody fragments include diabodies, single-chain antibody molecules, and multispecific antibodies formed from antibody fragments. scFv antibodies are, e.g., described in Huston, J. S., Methods in Enzymol. 203 (1991) 46-88. In addition, antibody fragments comprise single chain polypeptides having the characteristics of a $V_H$ domain, namely being able to assemble together with a $V_L$ domain, or of a $V_L$ domain binding to IGF-1, namely being able to assemble together with a $V_H$ domain to a functional antigen binding site and thereby providing the properties of an antibody according to the invention.

The terms "monoclonal antibody" or "monoclonal antibody composition" as used herein refer to a preparation of antibody molecules of a single amino acid composition.

The term "specific binding agent" is used to indicate that an agent is used which is able to either specifically bind to or to be specifically bound by an analyte of interest. Many different assay set-ups for immunoassays are known in the art. Dependent on the specific assay set-up, various biotinylated specific binding agents can be used. In one embodiment the biotinylated specific binding agent is selected from the group consisting of a biotinylated analyte-specific binding agent, a biotinylated analyte bound to solid phase, and a biotinylated antigen bound to solid phase.

The term "analyte-specific binding agent" refers to a molecule specifically binding to the analyte of interest. An analyte-specific binding agent in the sense of the present disclosure typically comprises binding or capture molecules capable of binding to an analyte (other terms analyte of interest; target molecule). In one embodiment the analyte-specific binding agent has at least an affinity of $10^7$ l/mol for its corresponding target molecule, i.e. the analyte. The analyte-specific binding agent in other embodiments has an affinity of $10^8$ l/mol or even of $10^9$ l/mol for its target molecule. As the skilled artisan will appreciate the term specific is used to indicate that other biomolecules present in the sample do not significantly bind to the binding agent specific for the analyte. In some embodiments, the level of binding to a biomolecule other than the target molecule results in a binding affinity which is only 10%, more preferably only 5% of the affinity of the target molecule or less. In one embodiment no binding affinity to other molecules than to the analyte is measurable. In one embodiment the analyte-specific binding agent will fulfill both the above minimum criteria for affinity as well as for specificity.

The term "analyte-specific binding" as used in the context of an antibody refers to the immunospecific interaction of the antibody with its target epitope on the analyte, i.e. the binding of the antibody to the epitope on the analyte. The concept of analyte-specific binding of an antibody via its epitope on an analyte is fully clear to the person skilled in the art.

The terms "polypeptide," "peptide" and "protein" refer to a polymer of amino acid residues. The terms apply to naturally occurring amino acid polymers as well as amino acid polymers in which one or more amino acid residues are a non-naturally encoded amino acid. As used herein, the terms encompass amino acid chains, wherein the amino acid residues are linked by covalent peptide bonds. The polypeptides, peptides and proteins are written using standard sequence notation, with the nitrogen terminus being on the left and the carboxy terminus on the right. Standard single letter notations have been used as follows: A-alanine, C-cysteine, D-aspartic acid, E-glutamic acid, F-phenylalanine, G-glycine, H-histidine, S-Isoleucine, K-lysine, L-leucine, M-methionine, N-asparagine, P-proline, Q-glutamine, R-arginine, S-serine, T-threonine, V-valine, W-tryptophan, Y-tyrosine. The term "peptide" as used herein refers to a polymer of amino acids that has a length of up to 5 amino acids. The term "polypeptide" as used herein refers to a polymer of amino acids that has a length of 6 or more amino acids. The term "protein" either signifies a polypeptide chain or a polypeptide chain with further modifications such as glycosylation, phosphorylation, acetylation or other post-translational modifications.

"Haptens" are small molecules (e.g. pesticides, fungicides, drugs, hormones, toxins, synthetic peptides, etc.) which do not directly induce an immune response such as formation of antibodies. Techniques have been established to raise antibodies against haptens by conjugating them with immunogenic carriers, such as antigenic macromolecules. For the purpose of the present disclosure, a hapten is understood as being a low molecular weight molecule, specifically having a molecular weight of 10,000 Da or less, which does not elicit immune response until and unless conjugated with an immunogenic carrier, such as protein. Once the antibody is formed, it can bind to the hapten. Antibodies thus generated are useful in many fields, specifically in the development of immunodiagnostic kits or biosensors. Thus, the term "hapten" denotes a small molecule of 10,000 Da or less that can elicit an immune response only when attached to an immunogenic carrier such as a polypeptide of at least 30 amino acids. In this sense, and in an embodiment, a hapten is an incomplete antigen that cannot, by itself, promote antibody formation but that can do so when conjugated to a protein of at least 30 amino acids. Exemplary haptens are aniline, o-, m-, and p-aminobenzoic acid, quinone, histamine-succinyl-glycine (HSG), hydralazine, halothane, indium-DTPA, fluorescein, digoxigenin, theophylline, bromodeoxyuridine, steroid compounds and dinitrophenol. In a specific embodiment, the hapten is not biotin and does not contain a biotin moiety. In one specific embodiment the hapten is digoxigenin or theophylline or fluorescein or bromodeoxyuridine. A hapten in the context of the disclosure of the compound according to Formula I, a hapten as a moiety of the compound is understood as a which is covalently coupled to the remaining portion of the compound, wherein the hapten moiety (i.e. the chemical structure of 10,000 Da or less) is capable of eliciting an immune response only when attached to an immunogenic carrier such as a polypeptide of at least 30 amino acids.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified to greater than 95% by weight of antibody, and in some embodiments, to greater than 99% as determined by SDS-PAGE under reducing or nonreducing conditions using, for example, Coomassie blue or silver stain.

Antibodies of the immunoglobulin G class usually are heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light-chain and heavy-chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, MD(1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (2), based on the amino acid sequences of their constant domains.

The antibodies used in a method according to the present invention may be from any animal origin. In one embodiment the antibodies are human, murine (e. g., mouse and rat), donkey, monkey, rabbit, goat, guinea pig, camel, horse, or chicken antibodies.

Depending on the amino acid sequences of the constant domains of their heavy chains, antibodies (immunoglobulins) can be assigned to different classes. There are five major classes of human immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called «, 8, E, Y, and u, respectively. The subunit structures and three-dimensional configurations of different classes of immunoglobulins are well known and described generally in, for example, Abbas et al. Cellular and Mol. Immunology, 4th ed. (W. B. Saunders, Co., 2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen-binding region thereof. Examples of antibody fragments include Fab, Fab', F(ab') 2, and Fv fragments; single-chain antibody molecules; scFv, sc (Fv) 2; diabodies; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab') 2 fragment that has two antigen-combining sites and is still capable of cross-linking antigen.

The Fab fragment contains the heavy- and light-chain variable domains and also contains the constant domain of the light chain and the first constant domain ($CH_1$) of the heavy chain. Fab' fragments differ from Fab fragments by the addition of a few residues at the carboxy terminus of the heavy chain CHI domain including one or more cysteines from the antibody-hinge region. Fab'-SH is the designation herein for Fab' in which the cysteine residue(s) of the constant domains bear a free thiol group. F(ab') 2 antibody fragments originally were produced as pairs of Fab' fragments which have hinge cysteines between them. Other chemical couplings of antibody fragments are also known.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv(scFv) species, one heavy- and one light-chain variable domain can be covalently linked by a flexible peptide linker such that the light and heavy chains can associate in a "dimeric" structure analogous to that in a two-chain Fv species (sc(Fv)2). It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The present disclosure includes monovalent Fab fragments and single chain Fv that are derived from monoclonal antibodies capable of specifically binding free biotin as disclosed in here. Compared with naturally occurring antibody forms the monovalent species can diffuse faster in aqueous solution, owing to their smaller molecular weight. Another aspect is that under suitable conditions particularly scFv antibodies can be recombinantly produced in prokaryotic expression systems.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404097; WO 1993/01161; Hudson et al., Nat. Med. 9:129-134 (2003); and Holliger et al., *PNAS USA* 90:6444-6448 (1993). Triabodies and tetrabodies are also described in Hudson et al., Nat. Med. 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature,* 256:495-97 (1975); Hongo et al., Hybridoma, 14 (3): 253-260 (1995), Harlow et al., *Antibodies: A Laboratory Manual,* (Cold Spring Harbor Laboratory Press, 2nd ed. 1988); Haemmerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352:624-628 (1991); Marks et al., *J. Mol. Biol.* 222:581-597 (1992); Sidhu et al., *J. Mol. Biol.* 338 (2): 299-310 (2004); Lee et al., *J. Mol. Biol.* 340 (5): 1073-1093 (2004); Fellouse, *PNAS USA* 101 (34): 12467-12472 (2004); and Lee et al., *J. Immunol. Methods* 284 (1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *PNAS USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and U.S. Pat. No. 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, Intern. Rev. Immunol.13:65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (e.g., U.S. Pat. No. 4,816,567 and Morrison et al., *PNAS USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

The term "hypervariable region," "HVR," or "HV," when used herein refers to the regions of an antibody-variable domain which are hypervariable in sequence and/or form structurally defined loops. Generally, antibodies comprise six HVRs; three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. See, e.g., Xu et al. *Immunity* 13:37-45 (2000); Johnson and Wu in *Methods in Molecular Biology* 248:1-25 (Lo, ed., Human Press, Totowa, NJ, 2003). Indeed, naturally occurring camelid antibodies consisting of a heavy chain only are functional and stable in the absence of light chain. See, e.g., Hamers-Casterman et al., Nature 363:446-448 (1993) and Sheriff et al., Nature Struct. Biol. 3:733-736 (1996).

A number of HVR delineations are in use and are encompassed herein. The HVRs that are Kabat complementarity-determining regions (CDRs) are based on sequence variability and are the most commonly used (Kabat et al., *Sequences of Proteins of Immunological Interest,* 5th Ed. Public Health Service, National Institutes of Health, Bethesda, MD(1991)). Chothia refers instead to the location of the structural loops (Chothia and Lesk *J. Mol. Biol.* 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (H2), and 93-102, 94-102, or 95-102 (H3) in the VH. The variable-domain residues are numbered according to Kabat et al., supra, for each of these extended-HVR definitions.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82*c*, etc. according to Kabat) after heavy-chain FR residue 82. The Kabat numbering of residues may be determined for a given antibody by alignment at regions of homology of the sequence of the antibody with a "standard" Kabat numbered sequence.

The term "experimental animal" denotes a non-human animal. In one embodiment the experimental animal is selected from rat, mouse, hamster, rabbit, camel, llama, non-human primates, sheep, dog, cow, chicken, amphibians, sharks and reptiles. In one embodiment the experimental animal is a rabbit.

Owing to the substituent at the N'1 atom, a molecule according to Formula I is incompatible with a binding pocket of (strept)avidin because the essential tight interaction with the heterocyclic structure of biotin is sterically hindered. It is hypothesized that this structure also prevents the formation of antibodies binding to a conventionally biotinylated molecule of interest once a compound according to Formula I is used as an immunogen. The structure of derivatized biotin disclosed herein still preservers the "tail" aspect of biotin, and so it was hypothesized that comprised in an immunogen the derivatized diaminobiotin might be suited to generate desired monoclonal antibodies against biotin.

In fact, in one embodiment the monoclonal antibody according to the invention does not bind a conventionally biotinylated molecule, i.e. a molecule conjugated with biotin, wherein the carbon atom of the carboxyl function of the valeric acid side chain of the biotin moiety is covalently coupled to the molecule. In a specific embodiment, the antibody according to the invention does not bind to a compound of Formula II, also depicted in FIG. 3A.

Rather, the monoclonal antibody according to the invention binds to a compound of Formula I, wherein Y is $CH_2$ or C=O, X is O or $(CH_2)_n$, and n is an integer from 1 to 20, and R is either H, or Z-L, wherein L is a linker, and Z is a hapten. In a specific embodiment, the monoclonal antibody according to the invention binds to a compound of Formula III depicted in FIG. 3 B.

In a more specific embodiment, the binding affinity of the monoclonal antibody to the compound of Formula III is higher by a factor of at least 50 than the binding affinity to the compound of Formula II. In yet another more specific embodiment, the binding affinity of the monoclonal antibody to the compound of Formula III is higher by a factor of at least 500, at least 1,000, at least 5,000, at least 10,000, at least 50,000, and at least 100,000 than the binding affinity to the compound of Formula II.

Thus, in another specific embodiment of all aspects as disclosed herein, the affinity of the monoclonal antibody for conjugated biotin on a biotinylated target molecule, including but not limited to the exemplary compound of Formula II (see FIG. 3A), is lower than the affinity for free biotin by a factor selected from the group consisting of at least 50, 100, 500, 1,000, 5,000, and at least 10,000. In other words, the monoclonal antibody according to the invention has an affinity for unconjugated (free) biotin which is higher than the affinity for conjugated biotin on a biotinylated target molecule by a factor selected from the group consisting of at least 50, 100, 500, 1,000, 5,000, and at least 10,000.

Numerous methods and systems have been developed for the detection and quantitation of analytes of interest in biochemical and biological samples. Methods and systems which are capable of measuring trace amounts of microorganisms, pharmaceuticals, hormones, viruses, antibodies, nucleic acids and other proteins are of great value to researchers and clinicians.

Many assay methods make use of an analyte-specific binding agent to capture a specific target molecule of interest from a sample, and allow for determination of the target molecule. In other assays an analyte of interest can be detected by competitive binding of a solid phase bound analyte and the analyte in the sample with a detectably labeled analyte-specific binding agent. In serological assays an antibody to an antigen, e.g. an infectious agent is detected directly or in a so-called double antigen sandwich assay.

Typically, the existence of an analyte of interest is indicated by the presence or absence of an observable "label" attached to one or more of the analyte-specific binding agents.

The vast majority of immunoassays nowadays one way or the other employs a solid phase. Usually at least one of the specific binding agents used in the assay is directly or indirectly bound to the solid phase. The (strept)avidin-biotin binding pair is characterized by an extremely high binding affinity. For this reason the (strept)avidin-biotin binding pair is broadly used for indirect binding of any appropriate biotinylated specific binding agents to a solid phase coated with (strept)avidin.

A "Sandwich assay" is an assay type which is among the most useful and commonly used assays. A number of variations of the sandwich assay technique exist, and all are intended to be encompassed by the present invention. Briefly, in a typical forward assay, an unlabeled antibody is immobilized on a "solid phase", and the sample to be tested is brought into contact with the bound molecule. Immobilization of this capture antibody can be by direct adsorption to a solid phase or indirectly, e.g. via a specific binding pair, e.g. via the streptavidin-biotin binding pair. After a suitable period of incubation, for a period of time sufficient to allow formation of an antibody-antigen complex, a second antibody binding to the antigen, labeled with a reporter molecule capable of producing a detectable signal is then added and incubated, allowing time sufficient for the formation of a sandwich-complex of antibody-antigen-labeled antibody. Any unreacted material is washed away, and the presence of the analyte is determined by observation of a signal produced by the reporter molecule. The results may either be qualitative, by simple observation of the visible signal, or may be quantitated by comparing with a control sample containing known amounts of analyte.

For the purpose of the present invention, in a typical sandwich assay a first biotinylated analyte specific binding agent, e.g. a biotinylated antibody is bound non-covalently to a solid phase, which is coated with (strept)avidin. The solid phase is typically glass or a polymer, the most commonly used polymers being cellulose, polyacrylamide, nylon, polystyrene, polyvinyl chloride, or polypropylene. The solid phase may be in the form of tubes, beads, discs of microplates, or any other surface suitable for conducting an immunoassay. Coating processes are well-known in the art and generally consist of cross-linking, covalent binding, or physically adsorbing. The (strept)avidin-coated solid phase is usually treated to block non-specific binding and washed in preparation for its in the testing procedure. An aliquot of the sample to be tested is contacted with the first or capture antibody and a labeled second antibody, and incubated for a period of time sufficient (e.g. 2-40 minutes or overnight if more convenient) and under suitable conditions (e.g., from room temperature to 40° C. such as between 25° C. and 32° C. inclusive) to allow for binding between the first or capture antibody and the corresponding antigen, and the antigen with the second antibody binding to another epitope on the antigen, thereby forming a sandwich complex.

Subsequently, the (strept)avidin-coated solid phase is added and incubated for a period of time sufficient (e.g. 2-40 minutes or overnight if more convenient) and under suitable conditions (e.g., from room temperature to 40° C. such as between 25° C. and 32° C. inclusive) to allow for binding between the first or capture antibody and the solid phase. The second antibody is linked to a reporter molecule which is used to indicate the binding of the second antibody to the complex of first antibody and the antigen of interest.

Variations on the assay include a simultaneous assay, in which both sample and labeled antibody are added simultaneously to the bound antibody or the antibody capable of being bound to the solid phase by means of a (strept)avidin/biotin binding pair. These techniques are well known to those skilled in the art, including any minor variations as will be readily apparent.

In a further alternative setting, a sandwich complex is formed, wherein a first biotinylated antibody is provided, a second antibody labeled with a hapten is provided, and the two antibodies are contacted with a sample containing the corresponding antigen. Upon incubation under conditions permissive with formation of a sandwich comprising the first and the second antibody, and the antigen, (strept)avidin carrying a label is added, and the complex is captured by a solid phase capable of specifically binding the hapten that is attached to the second antibody. After a washing step the amount of label bound by the solid phase indicates the presence and amount of the antigen of interest.

Generally, relating to all aspects and embodiments herein, the present disclosure provides a compound of Formula I,

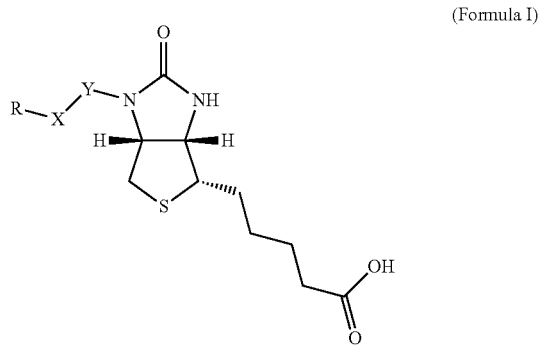

(Formula I)

wherein Y is $CH_2$ or C—O, X is an oxygen atom or $(CH_2)_n$ and n is an integer from 1 to 20, and R is either H, or Z-L, wherein L is a linker, and Z is selected from a hapten not containing a biotin moiety and a polypeptide.

A first key feature of the structure of Formula I is the biotin moiety with an unmodified, unconjugated valeric acid side chain. It was speculated that the conformation of the side chain relative to the heterocyclic structure of the biotin moiety is not totally random. This view seems to be corroborated by NMR data and the previous finding of an interaction between a carbon atom of the valeric acid side chain on the one hand, and the N'3 atom on the other hand. Thus, an unanswered question, so far, was whether the "tail" portion of the biotin molecule that is opposite to (distal from) the heterocyclic "head" portion which can be bound by (strept)avidin is actually suited for recognition by a monoclonal antibody.

The N'3 atom in the heterocyclic moiety of biotin in Formula I atom is another important feature, in that it is free of direct modification. Again, if this atom is involved in an interaction with a carbon atom being part of the valeric acid side chain, this interaction on the conformation of the side chain is likely preserved.

A further key feature which underlies the present invention is the N'1 atom of the heterocyclic moiety of biotin which carries the substituent R—X—Y, wherein Y is $CH_2$ or C—O, X is an oxygen atom or $(CH_2)_n$ and n is an integer from 1 to 20. Thus, substituted biotin is provided as a building block which allows, among other things, the formation of immunogens and of molecules useful for detecting and screening desired antibodies. Specifically for this purpose, the terminal group R can be selected to be Z-L, wherein L is a linker, and Z is selected from a hapten not containing a biotin moiety.

The term "linker" denotes a bifunctional or multifunctional moiety which can be used to conjugate (link) a first moiety with a second moiety or more moieties. Conjugates comprising a first and a second moiety bound to each other can be conveniently prepared using a linker having two reactive functionalities. In such conjugate the two moieties are bound "via" this linker. As obvious to the skilled artisan in such conjugate the functional moieties of the linker are present as part of a bond and not as an unreacted functional moiety.

As defined herein the term "reactive group" or "reactive functionality" means any group, which is suitable for reacting with amine groups, preferably an N-hydroxysuccinimide group or a maleimide group, in order to bind a linker to an amino group; or a group, which is suitable for a second functionality binding, e.g. for reacting with an SH-group, preferably a maleimide group in order to bind a linker to an SH-group.

In a specific embodiment, a heterobifunctional linker is selected from the group consisting of NHS-maleimide linkers, which are based on N-hydroxysuccinimide and maleimide reactive groups; succinimidyl-$(PEG)_n$ NHS-PEG-maleimide linkers, NHS-haloacetyl linkers; and NHS-pyridyldithiol linkers. In a particular preferred embodiment the heterobifunctional linker is a succinimidyl-$(PEG)_n$ NHS-PEG-maleimide linker.

In a specific embodiment, L has a backbone length of between 1 and 200 atoms. In other words if the backbone length is between 1 and 200 atoms, the shortest connection between Z and R consists of 1 to 200 atoms.

In case a ring system is present the shortest number of atoms in the ring system is taken when assessing the linker length. As an example, a phenylen ring accounts for a length of four atoms in a linker.

In one embodiment of Formula I, L is a linker having as a backbone a straight or branched saturated, unsaturated, unsubstituted or substituted C1-C20 alkyl chain, or a 1 to 200 atom chain consisting of carbon atoms, substituted carbon atoms and/or one or more atoms selected from O, N, P and S, or substituted N, P, S atoms, or a chain as described before with the backbone containing one or more cyclic or heterocyclic aromatic or non-aromatic ring systems.

In one embodiment of Formula I, the linker L has as a backbone a straight or branched saturated, unsaturated, unsubstituted or substituted C1-C100 alkyl chain, or a 1 to 100 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In one embodiment of Formula I, the linker L has as a backbone a straight or branched saturated, unsaturated, unsubstituted or substituted C1-C50 alkyl chain, or a 1 to 50 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In one further embodiment of Formula I, the linker L has as backbone a straight or branched saturated, unsaturated, unsubstituted or substituted C1-C20 alkyl chain, or a 1 to 20 atom chain consisting of carbon atoms, substituted carbon atoms and/or one or more atoms selected from O, N, P and S, or substituted N, P, or S atoms, or a chain as described before with the backbone containing one or more cyclic or heterocyclic aromatic or non-aromatic ring systems.

In another specific embodiment of Formula I, L is a linker, which is obtained upon reaction of a (homo-) bifunctional crosslinker with an appropriate chemical goup on each of the two moieties linked by the linker, the (homo-) bifunctional crosslinker is exemplified by

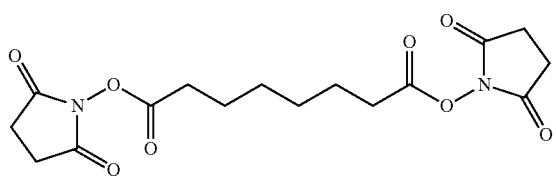 [SMILES: O=C(CCCCCCC(=O)ON1C(=O)CCC1=O)ON1C(=O)CCC1=O]

Octanedioic acid bis-(2,5-dioxo-pyrrolidin-1-yl) ester

In another specific embodiment of Formula I, L is a linker, which is obtained upon reaction of a (hetero-) bifunctional crosslinker with an appropriate chemical goup on each of the two moieties linked by the linker, the (hetero-) bifunctional crosslinker can be selected from the group consisting of NHS-maleimide crosslinkers, e.g.

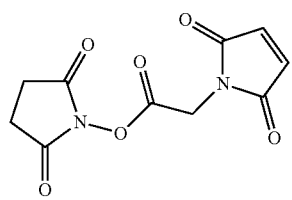

AMAS (N-α-maleimidoacet-oxysuccinimide ester)

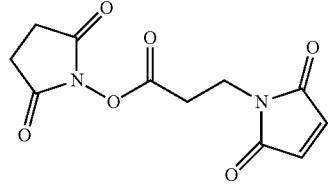

BMPS (N-β-maleimidopropyl-oxysuccinimide ester)

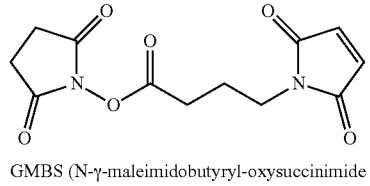

GMBS (N-γ-maleimidobutyryl-oxysuccinimide ester)

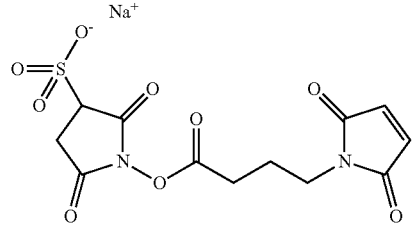

Sulfo-GMBS (N-γ-maleimidobutyryl-oxysuccinimide ester)

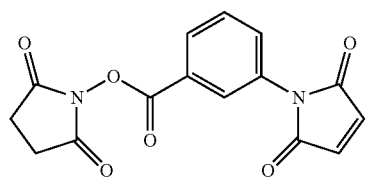

MBS (m-maleimidobenzoyl-N-hydroxysuccinimide ester)

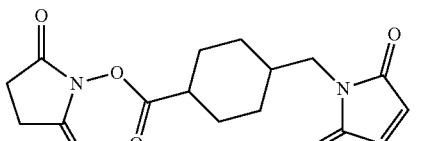

Sulfo-MBS (maleimidobenzoyl-N-hydroxysulfosuccinimide ester)

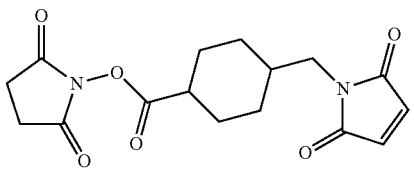

SMCC (succinimidyl 4-(N-maleimidomethyl)cyclohexane-1-carboxylate

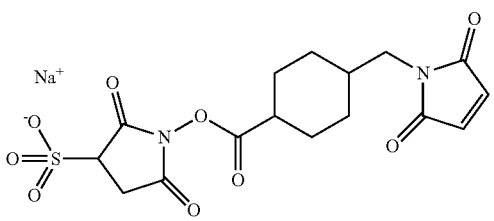

Sulfo-SMCC (sulfosuccinimidyl 4-(N-maleimidomethyl)cyclohexane-1-carboxylate

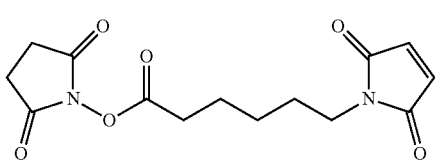

EMCS (N-ε-malemidocaproyl-oxysuccinimide ester)

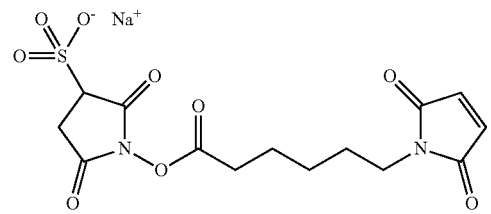

Sulfo-EMCS (N-ε-maleimidocaproyl-oxysulfosuccinimide ester)

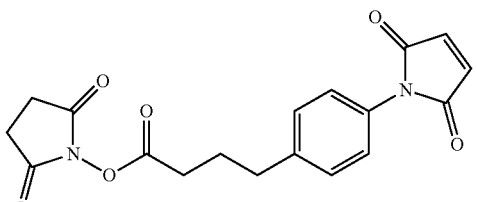

SMPB (succinimidyl 4-(p-maleimidophenyl)butyrate)

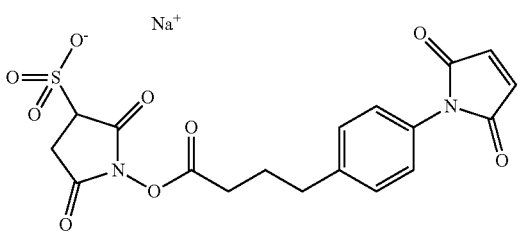

Sulfo-SMPB (sulfosuccinimidyl 4-(N-maleimidophenyl)butyrate)

-continued

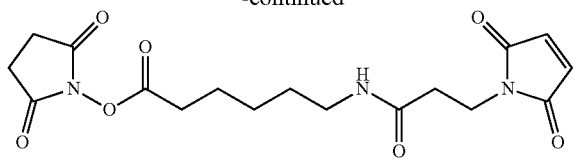

SMPH (Succinimidyl 6-((beta-maleimidopropionamido)hexanoate))

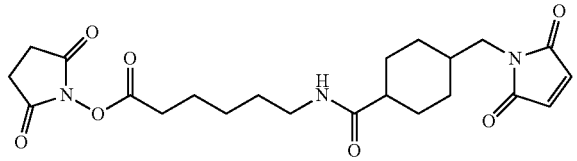

LC-SMCC (succinimidyl 4-(N-maleimidomethyl)cyclohexane-1-carboxy-(6-amidocaproate)

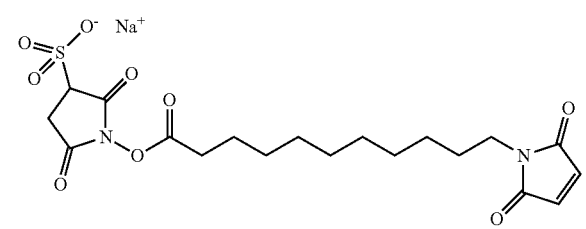

Sulfo-KMUS (N-K-maleimidoundecanoyl-oxysulfosuccinimide ester)

succinimidyl-(PEG) n-maleimide or NHS-PEG-maleimide crosslinkers, e.g.

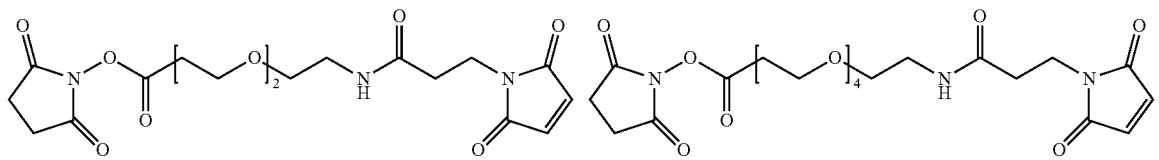

SM(PEG)2 (PEGylated SMCC crosslinker)
NHS-PEGn-Maleimide
Succinimidyl-([N-maleimidopropionamido]-di-ethyleneglycol) ester SM(PEG)4 (PEGylated SMCC crosslinker)
NHS-PEGn-Maleimide
Succinimidyl-([N-maleimidopropionamido]-tetra-ethyleneglycol) ester

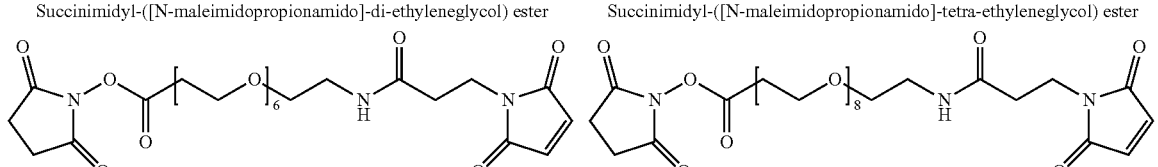

SM(PEG)6 (PEGylated, long-chain SMCC crosslinker)
NHS-PEGn-Maleimide
Succinimidyl-([N-maleimidopropionamido]-hexa-ethyleneglycol) ester SM(PEG)8 (PEGylated, long-chain SMCC crosslinker)
NHS-PEGn-Maleimide
Succinimidyl-([N-maleimidopropionamido]-octa-ethyleneglycol) ester

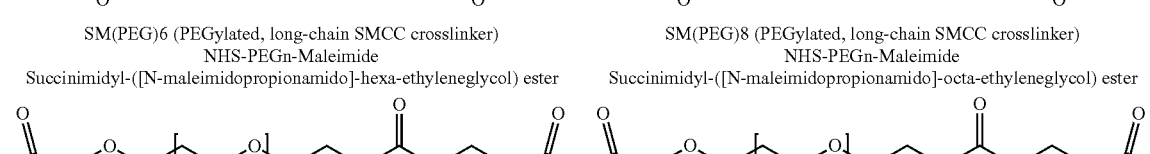

SM(PEG)12 (PEGylated, long-chain SMCC crosslinker)
NHS-PEGn-Maleimide
Succinimidyl-([N-maleimidopropionamido]-dodeca-ethyleneglycol) ester SM(PEG)24 (PEGylated, long-chain SMCC crosslinker)
NHS-PEGn-Maleimide
Succinimidyl-([N-maleimidopropionamido]-twentyfour-ethyleneglycol) ester NHS-haloacetyl crossliners, e.g.

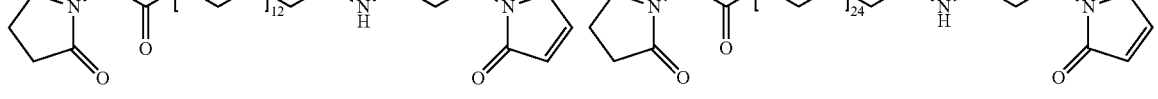

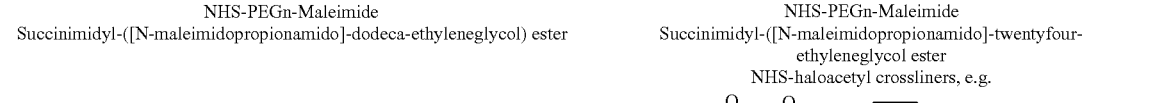

SIA (succinimidyl iodoacetate)    SBAP (succinimidyl 3-(bromoacetamido)propionate)    SIAB (succinimidyl (4-iodoacetyl)aminobenzoate)

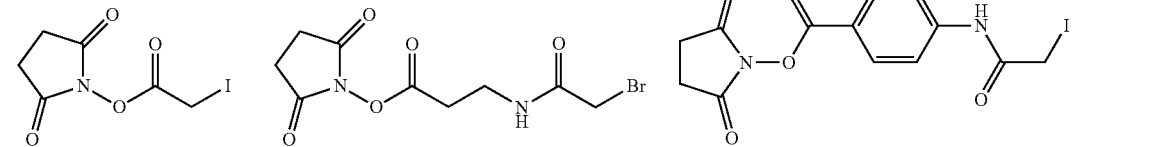

Sulfo-SIAB (sulfosuccinimidyl (4-iodoacetyl)aminobenzoate)    SPDP Succinimidyl 3-(2-pyridyldithiol)propionate)
and NHS-pyridyldithiol crosslinkers e.g.

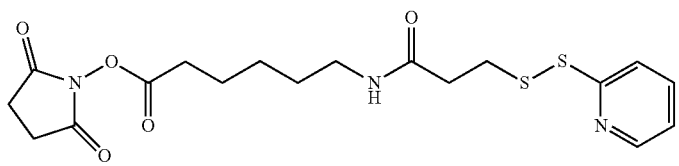

LC-SPDP Succinimidyl 6-[3(2-pyridyldithiol)propionamido]hexanoate

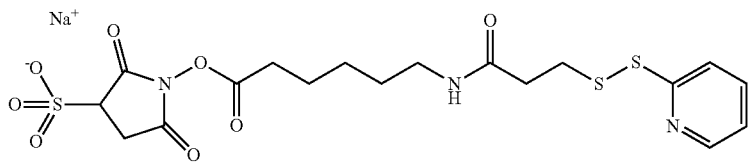

Sulfo-LC-SPDP (sulfosuccinimidyl 6-(3'-(2-pyridyldithio)propionamido)hexanoate

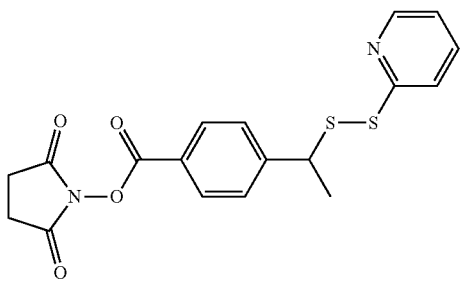

SMPT (4-succinimidyloxycarbonyl-alpha-methyl-a(2-pyridyldithio)toluene)

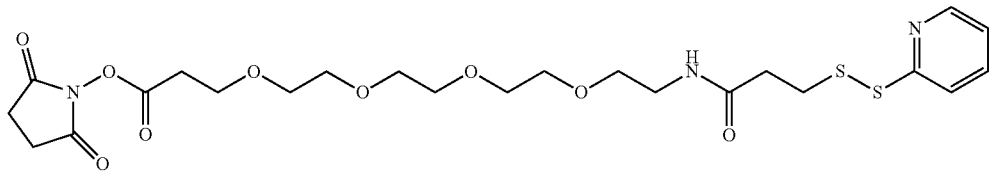

PEG4-SPDP (PEGylated, long-chain SPDP crosslinker)

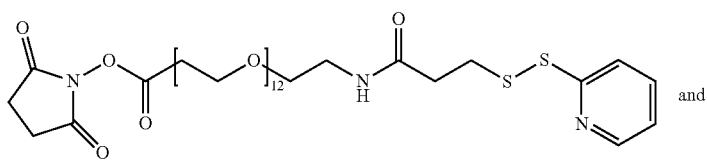

and

PEG12-SPDP (PEGylated, long-chain SPDP crosslinker)

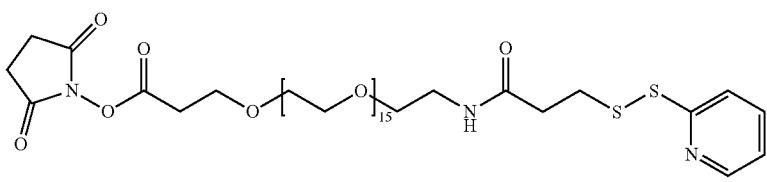

alpha-[3-(o-Pyridyldisulfido)propanoylamido]-omega-(succinimidyl propionate)hexadeca(ethylene glycol)

In an embodiment of Formula I R is Z-L, and Z is a polypeptide. Thus, another general aspect of the original disclosure herein, and of the invention, which is also related to all other aspects and embodiments as disclosed herein is an immunogen according to Formula I, wherein Y is $CH_2$ or $C=O$, X is O or $(CH_2)_n$ and n is an integer from 1 to 20, and R is Z-L, wherein L is a linker, and Z is a polypeptide of at least 30 amino acids.

Importantly, the polypeptide is capable of eliciting an immune response to the biotin moiety, while the immunogenicity of the biotin moiety alone is low. In an embodiment, the polypeptide is selected from rat, rabbit, mouse, porcine or bovine serum albumin, bovine or porcine thyroglobulin, ovalbumin, tetanus toxoid, gelatin, soybean trypsin inhibitor, keyhole limpet hemocyanin and similar substances. In a specific embodiment, the polypeptide is keyhole limpet hemocyanin (KLH).

In one embodiment the present disclosure related to all other aspects and embodiments also provides methods for making polyclonal antibodies (including antibodies, antibody fragments thereof, and antigen binding fragments thereof) that specifically bind to the immunogen according to the present disclosure. The method comprises: (a) providing an immunogen according to the invention; (b) immunizing an experimental animal with the immunogen under conditions such that the immune system of the animal makes the antibodies; and (c) removing the antibodies that specifically bind to biotin from the animal. The animal can be a sheep, goat, rabbit, rat, mouse and the like.

Another general aspect of the original disclosure herein, and of the invention, which is also related to all other aspects and embodiments as disclosed herein is a method of producing an antibody according to the invention, the method comprising the steps of (a) immunizing an experimental animal with an immunogen according to the invention, thereby inducing B-cells producing antibodies binding to the immunogen, (b) obtaining a monoclonal antibody binding to the immunogen produced by the B-cell of step (a), either via hybridoma technology or by B-cell PCR technology, (c) further selecting the antibody of step (b) for binding to biotin, thereby obtaining an antibody according to the invention.

In an embodiment, in Formula I, R is Z-L, and Z is a hapten, wherein the hapten does not contain a biotin moiety. Thus, another general aspect of the original disclosure herein, and of the invention, which is also related to all other aspects and embodiments as disclosed herein is a compound according to Formula I, wherein Y is $CH_2$ or $C=O$, X is O or $(CH_2)_n$ and n is an integer from 1 to 20, and R is Z-L, wherein L is a linker, and Z is a hapten, wherein the hapten does not contain a biotin moiety.

A compound according to this aspect is particularly useful in capturing desired antibodies, e.g. in a process of identifying polyclonal or monoclonal antibodies generated using an immunogen according to the invention. Such antibodies will specifically bind to the biotin moiety of the compound, that is to say the compound is capable of capturing the desired antibodies according to the invention. In this regard, the hapten must not be and/or must not contain a further biotin moiety, in order to maintain the capturing specificity of the compound. Thus, a suitable hapten which is not biotin and/or does not contain biotin is selected from the group consisting of dinitrophenol, aniline, aminobenzoic acid, hydralazine, fluorescein, and digoxigenin. In a specific embodiment, Z is digoxigenin.

A particular embodiment of a compound according to Formula I, wherein Y is $CH_2$ or $C=O$, X is O or $(CH_2)_n$ and n is an integer from 1 to 20, and R is Z-L, wherein L is a linker, and Z is a hapten, wherein the hapten does not contain a biotin moiety is the compound of Formula III.

(Formula III)

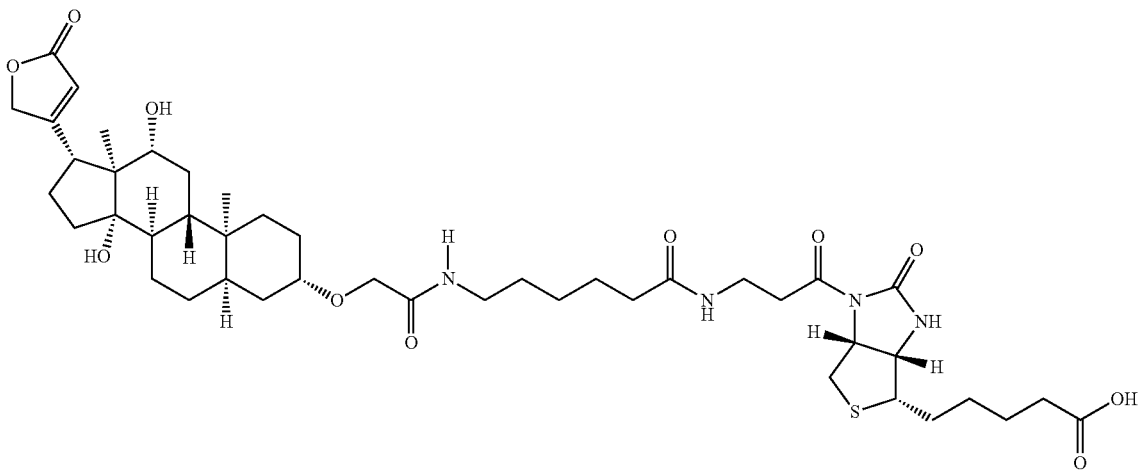

Another general aspect of the original disclosure herein, and of the invention, which is also related to all other aspects and embodiments as disclosed herein is a method of producing an antibody according to the invention, the method comprising the steps of (a) immunizing an experimental animal with an immunogen according to the invention, thereby inducing B-cells producing antibodies binding to the immunogen, (b) obtaining a monoclonal antibody binding to the immunogen produced by the B-cell of step (a), either via hybridoma technology or by B-cell PCR technology, (c) further selecting the antibody of step (b) for binding to biotin, thereby obtaining an antibody according to the invention.

The generation of cell lines which produce monoclonal antibodies by way of hybridoma technology is well known to the skilled person.

B-cell PCR technology known to the skilled person takes advantage from the fact that from B-cells the total mRNA can be isolated and transcribed to cDNA. With specific primers the cognate VH- and VL-region encoding nucleic acid can be amplified. Almost no identical sequences are obtained. The method provides for highly diverse antibodies binding to the same antigen.

The primers used for the amplification of the VH-encoding nucleic acid can be used for cDNA obtained from cells from the NMRI-mouse, the Armenian Hamster, the Balb/c-mouse as well as the Syrian hamster and the rabbit.

In one embodiment of all methods as reported herein the amino acid sequence is derived from the amplified VH-encoding nucleic acid and the exact start and end point is identified by locating the amino acid sequences of EVQL/QVQL to VSS (VH-region) and DIVM/DIQM to KLEIK (VL-region).

Also reported herein is a method using B-cell PCR for producing an antibody comprising the following steps: (a) providing a population of (mature) B-cells (obtained from the blood of an experimental non-human animal), (b) staining the cells of the population of B-cells with at least one fluorescence dye (in one embodiment with one to three, or two to three fluorescence dyes), (c) depositing single cells of the stained population of B-cells in individual containers (in one embodiment is the container a well of a multi well plate), (d) cultivating the deposited individual B-cells in the presence of feeder cells, (e) determining the binding specificity of the antibodies secreted in the cultivation of the individual B-cells, (f) determining the amino acid sequence of the variable light and heavy chain domain of specifically binding antibodies by a reverse transcriptase PCR and nucleotide sequencing, and thereby obtaining a monoclonal antibody variable light and heavy chain domain encoding nucleic acid, (g) introducing the monoclonal antibody light and heavy chain variable domain encoding nucleic acid in an expression cassette for the expression of an antibody, (h) introducing the nucleic acid in a cell, (i) cultivating the cell and recovering the antibody from the cell or the cell culture supernatant and thereby producing an antibody.

In one embodiment the non-human animal is selected from rat, mouse, hamster, rabbit, non-human primates, sheep, dog, cow, chicken, amphibians, and reptiles.

In a specific embodiment of the herein disclosed method for producing a monoclonal antibody, in step (c) the selection is performed in a competitive assay using biotin as a competitor for binding of the antibody to a compound according to Formula I, wherein Y is $CH_2$ or C=O, X is O or $(CH_2)_n$ and n is an integer from 1 to 20, and R is either H, or Z-L, wherein L is a linker, and Z is selected from a hapten not containing a biotin moiety and a polypeptide.

This compound has been discussed above, already. The compound is particularly useful in capturing desired antibodies. Such antibodies will specifically bind to the biotin moiety of the compound, that is to say the compound is capable of capturing the desired antibodies according to the invention. In this regard, the hapten must not be and/or must not contain a further biotin moiety, in order to maintain the capturing specificity of the compound. Thus, the hapten is used to anchor the capture reagent on a solid phase, e.g. as exemplified with digoxigenin as the hapten in Example 5.

Another important step is the selection and/or confirmation that an antibody, specifically a monoclonal antibody generated using an immunogen as disclosed herein, and by a method as disclosed herein is actually capable of binding biotin. A competitive binding assay thereby ensures that the antibody is capable of binding biotin when contacted with free biotin in aqueous solution. Accordingly, in an embodiment of the herein disclosed method for producing a monoclonal antibody in step (c) the selection is performed in a competitive assay using biotin as a competitor for binding of the antibody to the immunogen as disclosed herein.

Figure 3B:
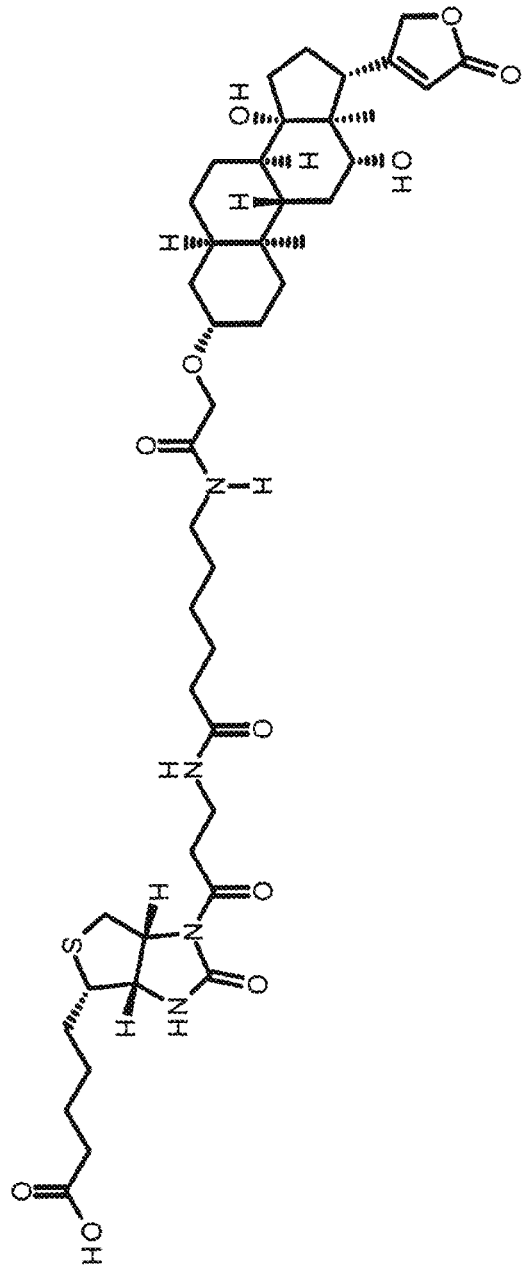

In another embodiment of the herein disclosed method for producing a monoclonal antibody in step (c) the selection is performed in a competitive assay using biotin as a competitor for binding of the antibody to the to a compound of Formula III, also depicted in FIG. 3 B.

More generally, in another embodiment of the herein disclosed method for producing a monoclonal antibody in step (c) the selection is performed in a competitive assay using biotin as a competitor for binding of the antibody to the to a compound according to Formula I, wherein Y is $CH_2$ or C=O, X is O or $(CH_2)_n$ and n is an integer from 1 to 20, and R is Z-L, wherein L is a linker, and Z is a hapten, wherein the hapten does not contain a biotin moiety.

As evidenced in the Examples of present disclosure, the invention in its aspects and embodiments now provides a novel monoclonal antibody specifically binding a compound of Formula I,

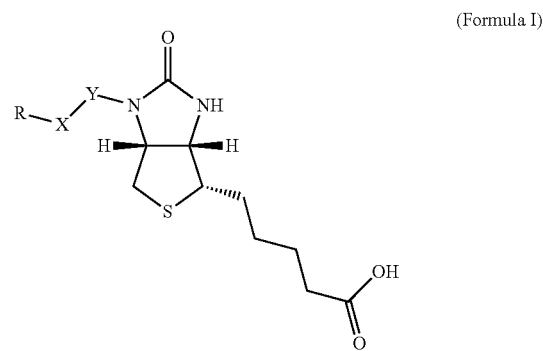

(Formula I)

characterized in that it also binds to biotin, wherein Y is $CH_2$ or C=O, X is O or $(CH_2)_n$ and n is an integer from 1 to 20, and R is either H, or Z-L, wherein L is a linker, and Z is selected from a hapten not containing a biotin moiety and a polypeptide.

The monoclonal antibody of the invention can be obtained by a method according to the invention and as disclosed herein.

As described above, the monoclonal antibody according to the invention is characterized in that it does not bind a compound of Formula II. In Formula II the biotin moiety is coupled via a linker to a hapten via carbon atom of the carboxyl function of the valeric acid side chain. Thus the molecule exemplifies a conventionally biotinylated molecule to which the desired antibodies according to the invention do not bind.

Thus, another general aspect of the original disclosure herein, and of the invention, which is also related to all other aspects and embodiments as disclosed herein is a method for producing an antibody which does not bind to a biotinylated molecule, wherein the biotin moiety is coupled via a linker to a hapten via carbon atom of the carboxyl function of the valeric acid side chain, the method comprising the steps of (a) immunizing an experimental animal with an immunogen according to the invention, thereby inducing B-cells producing antibodies binding to the immunogen, (b) obtaining a monoclonal antibody binding to the immunogen produced by the B-cell of step (a), either via hybridoma technology or by B-cell PCR technology, (c) selecting the antibody of step (b) for binding to biotin, and (d) selecting those antibodies which do not bind to the biotinylated molecule, thereby obtaining an antibody according to the invention which does not bind to a biotinylated molecule. In a specific embodiment, step (d) is performed with a compound according to Formula II.

Thus, more specifically, there is disclosed a method for producing an antibody which does not bind to a compound of Formula II, the method comprising the steps of (a) immunizing an experimental animal with an immunogen according to the invention, thereby inducing B-cells producing antibodies binding to the immunogen, (b) obtaining a monoclonal antibody binding to the immunogen produced by the B-cell of step (a), either via hybridoma technology or by B-cell PCR technology, (c) selecting the antibody of step (b) for binding to biotin, and (d) selecting those antibodies which do not bind to the compound of Formula II, thereby obtaining an antibody according to the invention which does not bind to a compound according to Formula II.

Particularly in a method for measuring an analyte in a sample, wherein a (strept)avidin/biotin binding pair is used to bind a biotinylated analyte specific binding agent to a (strept)avidin coated solid phase, the measurement of the analyte may become inaccurate if the sample contains extraordinary high amounts of biotin. For this reason it is highly desired to scavenge biotin. This technical problem can be solved by sample pre-treatment, i.e. with a process of removing free biotin before the sample is subjected to the method for measuring the analyte. However, this would involve an undesired large number of discrete working steps such as, e.g., mixing the sample with magnetic particles that are coated with (strept)avidin, incubating the mixture thereby binding the biotin to the particles, followed by magnetically removing the particles. Not only is such an approach of sample pre-treatment consuming resources such as raw materials and time; in addition such an approach bears the risk of changing the sample (e.g. its volume and composition) which in turn may lead to undesired effects in analyte detection and measurement.

Surprisingly it was found that a monoclonal antibody according to the invention capable of binding biotin and not binding to conventionally biotinylated molecules of interest provide for elegant solution to reduce biotin interference. While acting as a biotin scavenger, the biotin binding property of the antibody is such that it does not interfere with the binding of e.g. a biotinylated analyte specific binding agent to (strept)avidin. Thus, the monoclonal antibody according to the invention turns out to be a powerful tool in counteracting interference caused by a high level of biotin that might be present in the sample.

Another general aspect of the original disclosure herein, and of the invention, which is also related to all other aspects and embodiments as disclosed herein is the use of an antibody according to the invention, in a method for measuring an analyte in a sample, wherein a (strept)avidin/biotin pair is used to bind a biotinylated analyte specific binding agent to a (strept)avidin coated solid phase.

Another general aspect of the original disclosure herein, and of the invention, which is also related to all other aspects and embodiments as disclosed herein is a method for measuring an analyte in a sample, wherein a (strept)avidin/biotin binding pair is used to bind a biotinylated analyte specific binding agent to a (strept)avidin coated solid phase, the method comprising adding to the sample a) an antibody according to the invention, b) a biotinylated analyte specific binding agent, c) a streptavidin coated solid phase, followed by measuring the analyte bound to the solid phase via (strept)avidin and biotinylated analyte specific binding agent.

The present disclosure provides the means to scavenge potentially interfering free biotin comprised in a sample from which sample an analyte shall be measured and which measuring method makes use of the (strept)avidin/biotin binding pair. Preferred the scavenging step is performed prior to the formation of the (strept)avidin/biotin pair. Thus, in an embodiment there is provided a method for measuring an analyte in a sample, wherein a (strept)avidin/biotin binding pair is used to bind a biotinylated analyte specific binding agent to a (strept)avidin coated solid phase, the method comprising adding to the sample a) an antibody according to the invention, b) a biotinylated analyte specific binding agent, c) a (strept)avidin coated solid phase, followed by measuring the analyte bound to the solid phase via (strept)avidin and biotinylated analyte specific binding agent, wherein step (a) and optionally also step (b) is performed before step (c). In yet another embodiment, step (a) and step (b) are performed simultaneously before step (c) is performed. In yet another embodiment, step (b) and step (c) are performed simultaneously after step (a) has been performed. In yet another embodiment, all three steps (a), (b) and (c) are performed simultaneously. Surprisingly, a monoclonal antibody of the invention is even technically suited as an effective scavenger for free biotin for the use in a method for measuring an analyte in a sample, the sample containing free biotin, wherein a (strept)avidin/biotin pair is used to bind a biotinylated analyte specific binding agent to a (strept)avidin coated solid phase or to a labelled (strept)avidin, wherein the sample, the monoclonal antibody of the invention, a biotinylated binding agent and either of a (strept)avidin coated solid phase or a labeled stereptavidin are contacted with each other simultaneously.

Concerning all aspects and embodiments of analyte detection and/or measurement as disclosed herein an aqueous liquid sample can be used in a method for specific in vitro-detection of an analyte in a method according to the present disclosure. The sample may be known to comprise the analyte or it may be suspected of comprising the analyte. In one embodiment a sample for in vitro diagnosis used in a method according to the present disclosure is a body fluid selected from whole blood, blood serum, blood plasma, liquor, urine or saliva. In one embodiment the sample suspected of comprising or comprising the analyte is serum, plasma or liquor. In one embodiment the sample suspected of comprising or comprising the analyte is serum or plasma.

Another general aspect of the original disclosure herein, and of the invention, which is also related to all other aspects and embodiments as disclosed herein is an immunoassay test kit comprising in separate containers at least (a) an antibody according to any of claims according to the invention, (b) a biotinylated analyte specific binding agent, and (c) a (strept) avidin coated solid phase.

The term single container unit relates to the fact that for many automatic analyzers, like the Elecsys® analyzer series from Roche diagnostics, the reagents required to measure a certain analyte are provide in the form of a "reagent pack", i.e. as one container unit fitting on the analyzer and containing in different compartments all the key reagents required for measurement of the analyte of interest.

In one embodiment the present invention relates to a kit wherein said first partner of a binding pair is avidin or streptavidin, and wherein said second partner of said binding pair is selected from biotin or biotin analogues such as aminobiotin, iminobiotin or desthiobiotin.

The following examples and figures are provided to aid the understanding of the present invention, the true scope of which is set forth in the appended claims. It is understood that modifications can be made in the procedures set forth without departing from the spirit of the invention.

Example 1

Derivatization of Biotin at the N'1 Atom (1) FMOC-beta-alanine-acid chloride

To 4.7 g FMOC-beta-alanine (IRIS, FAA1300) in a flask under dry conditions ca. 20 mL thionyl chloride were added slowly. The mixture was stirred at room temperature for 50 min. and afterwards heated to reflux for 10 min. After cooling, the mixture was evaporated, the residue was dissolved in absolute toluene three times and evaporated each time.

The yield was 5.1 g.

(2) FMOC-Beta-Alanyl-Biotin

The carboxylic acid of biotin was protected by reacting biotin (2.48 g) with t-butylchlorodiphenylsilane (6.5 ml) in 15 mL dry pyridine in the presence of DMAP (0.63 g) overnight at room temperature in an inert atmosphere of argon as described by Fang and Bergstrom in Nucleic Acids Research, 2003, Vol. 31, No. 2, 708.

4.9 g FMOC-beta-alanine-acid chloride dissolved in 10 mL dichloromethane were added and stirred for 3.5 h at room temp. The mixture was evaporated, DMF added and evaporated again. The residue was dissolved in DMF-$H_2O$ (3:1) and 50 mmol potassium carbonate was added and the mixture was stirred for 30 min. After acidification with citric acid to pH 4 the product was extracted with ethyl acetate and purified by column chromatography (silica, eluent ethyl acetate/methanol).

HPLC-ESI-MS: $M^+$=538.3 Da. The yield was 1.5 g.

(3) Beta-alanyl-biotin=5-[3-(3-Amino-propionyl)-2-oxo-hexahydro-thieno[3,4-d]imidazol-6-yl]-pentanoic acid The FMOC protecting group was cleaved by dissolving 1.67 g FMOC-beta-alanyl-biotin in a mixture of 20% piperidine in DMF (60 ml). The mixture was evaporated and dried under vacuum.

Afterwards the product was isolated by prep HPLC using reverse phase silica and a $H_2O$-acetonitrile gradient.

HPLC-ESI-MS: $M^+$=316.3 Da. The yield was 0.55 g.

Example 2

Synthesis of immunogen (4) Succinimidyl-suberyl-beta-alanyl-biotin=7-{3-[6-(4-Carboxy-butyl)-2-oxo-hexahydro-thieno[3,4-d]imidazol-3-yl]-3-oxo-propylcarbamoyl}-heptanoic acid 2,5-dioxo-pyrrolidin-1-yl ester 24 mg Disuccinimidyl suberate and 10 µl trimethylamine were added to a 10 mL flask and afterwards 10 mg beta-alanyl-biotin dissolved in 1 mL DMF were added. After stirring for 30 min the solvent was removed under vacuum. The residue was purified by preparative HPLC.

HPLC-ESI-MS: $M^+$=569.3 Da. The yield was 12 mg.

(5) Antigen conjugate=KLH-SUB-beta-ala-biotin 10 mg of the NHS ester synthesized as described above in Example 1 was dissolved in 1000 µl DMSO and added to a solution of 100 mg KLH (Keyhole Limpet Hemocyanin, Sigma H 8283). The pH was adjusted to pH=8.3 and the solution stirred overnight. The mixture was purified in an Amicon stirred cell.

Analytics of amino groups: Antigen-KLH ratio-ca. 500:1

Example 3

Synthesis of Reagents for the Screening of Monoclonal Antibodies (1) Dig-3-CME-AMCAP-DADOO-biotin Digoxigenin-3-CME-AMCAP-NHS ester (other names: Digoxigenin NHS-Ester, Card-20 (22)-enolide, 3-[2-[[6-[(2,5-dioxo-1-pyrrolidinyl)oxy]-6-oxohexyl]amino]-2-oxoethoxy]-12,14-dihydroxy-, (3β,5β,12β)-)=CAS Nr. 129273-26-3 was synthesized as described in DE3836656A1, or was obtained as commercially available product (Merck-Sigma).

21 mg Digoxigenin-3-CME-AMCAP-NHS ester were dissolved in 3 mL DMF and 6 µl trimethylamine were added. Afterwards 14 mg Biotin-DADOO were added and the mixture was stirred at room temp. for 2 h. The solvent was removed by evaporation and the product was isolated by preparative HPLC chromatography.

HPLC-ESI-MS: $M^+$=918.7 Da. Yield: 23 mg.

(2) Dig-3-CME-AMCAP-beta-ala-biotin

Beta-alanyl-biotin=beta-ala-biotin=5-[3-(3-Amino-propionyl)-2-oxo-hexahydro-thieno[3,4-d]imidazol-6-yl]-pentanoic acid was synthesized as described above (Example 1).

Digoxigenin-3-CME-AMCAP-NHS ester (other names: Digoxigenin NHS-Ester, Card-20 (22)-enolide, 3-[2-[[6-[(2,5-dioxo-1-pyrrolidinyl)oxy]-6-oxohexyl]amino]-2-oxoethoxy]-12,14-dihydroxy-, (3,58,12β)-)=CAS Nr. 129273-26-3 was synthesized as described in DE3836656A1, or was obtained as commercially available product (Merck-Sigma).

20 mg Digoxigenin-3-CME-AMCAP-NHS ester were dissolved in 3 mL DMF and 6 µl triethylamine were added. Afterwards 10.5 mg beta-ala-biotin were added and the mixture was stirred at room temp. for 3.5 h. The solvent was removed by evaporation and the product was isolated by prep. HPLC chromatography.

HPLC-ESI-MS: $M^+$=859.6 Da. Yield: 16 mg.

Example 4

Immunization of Rabbits for Generation of Antibodies Binding Free-Biotin

In the present disclosure there is reported the development of antibodies with the ability to scavenge free biotin. To this end we generated antibodies which bind to biotin only if the COOH-group of the valeric acid moiety of biotin is accessible and not used for conjugation. The antibodies according to the invention do not bind to biotinylated molecules, i.e. conventional biotin-conjugates where biotin is covalently coupled via the carbon atom of the carboxyl group.

For the generation of such antibodies, 12-16-weeks old NZW rabbits were immunized with KLH-SUB-beta-ala-biotin (see above, Example 2). All rabbits were subjected to repeated immunizations. In the first month the animals were immunized weekly. From the second month onward the animals were immunized once per month. For the first immunization 500 µg KLH-SUB-beta-ala-biotin was dissolved in 1 mL 140 mM NaCl and was emulsified in 1 mL CFA (complete Freund's adjuvans). For all following immunizations, CFA was replaced by IFA (incomplete Freund's adjuvans). The titers of the animals were evaluated on day 45 after start of the immunization.

Example 5

Antibody Titer Analysis of the Immunized Animals

The experimental setup of serum titrations was designed to determine the amount of polyclonal antibodies that can discriminate between (i) a conjugated biotin of the conventional type, i.e. a biotin that is conjugated to the carrier via the carbon atom of the carboxyl function of the valeric acid moiety, and (ii) a conjugated biotin of which the N'1 atom of the ureido ring is covalently attached to a carrier. Example 3 and FIGS. 3A and B provide the compounds (1) Dig-3-CME-AMCAP-DADOO-biotin (compound of Formula II) exemplary for (i), and (2) Dig-3-CME-AMCAP-beta-ala-biotin (compound of Formula III) exemplary for (ii).

Therefore 96well plates were first coated with 5 µg/mL of a polyclonal sheep anti-Dig antibody (Sigma). After a washing step, the plates were blocked with 5% BSA (Roche) to reduce background signals. To capture the different biotin-Dig conjugates (CME-AMCAP-beta-ala-biotin and Dig-3-CME-AMCAP-DADOO-biotin) the anti-Dig coated plates were incubated with 250 ng/ml of the conjugates, in separate wells. After an additional washing step, the rabbit sera were diluted in PBS with 1% BSA, and the dilutions were added to the plates. The sera were tested at dilutions 1:300, 1:900, 1:2,700, 1:8,100, 1:24,300, 1:72,900, 1:218,700 and 1:656,100. Bound antibody was detected with a HRP-labeled F(ab) 2 goat anti-rabbit Fcγ (Dianova) and ABTS (Roche) as a substrate. The titer of the analyzed animals was set by 50% signal decrease of the dilution curve.

As additional negative controls, the plates were also coated with different conventionally biotinylated molecules, a peptide-biotin conjugate (CD68-bi), a recombinant protein-biotin conjugate (CD4-bi) and a recombinant F(ab') 2-biotin conjugate rK-F(ab) 2. In all of the 3 negative controls, biotin was coupled to the linker via the carbon atom of the carboxyl function of the valeric acid moiety and therefore should not be detected by the polyclonal sera. Table 2 shows the results.

TABLE 2

Titration of the sera of experimental animals immunized with the Biotin-KLH immunogen, wherein Biotin is coupled to KLH via N'$_1$ atom of the ureido ring.

| animal | rK-F(ab')2 | CD68-bi (peptide) | CD4-bi (protein) | Compound Formula III | Compound Formula II |
|---|---|---|---|---|---|
| 1#E24273 | — | — | — | 124245 | 757 |
| 2#E24279 | — | — | — | 124814 | 667 |
| 3#E24281 | 3055 | — | — | 138535 | 709 |

It is shown, that the polyclonal sera from the 3 immunized animals only bind Dig-3-CME-AMCAP-beta-ala-biotin, which is similar to the immunogen and were the COOH-group of the valeric acid side chain is accessible. All screening reagents in which biotin is coupled via to the respective carrier via the carbon atom of the carboxyl function of the valeric acid moiety, rK-F(ab) 2, CD68-bi, CD4-bi and Dig-3-CME-AMCAP-DADOO-biotin were detected only weakly or not at all.

Example 6

Development of Monoclonal Antibodies Binding Free-Biotin

For the development of antibodies capable of binding to biotin in solution (i.e. free biotin) and without cross reactivity conventionally biotinylated targets, B-cell cloning as described in Seeber et al. (2014), PLOS One. 2014 Feb. 4; 9 (2) was used. For the enrichment of antigen reactive B-cells a biotinylated mouse anti-Dig antibody (Roche) was bound to streptavidin coated magnetic beads (Miltenyi). Afterwards, the PBMC pool of the immunized animals was prepared and incubated with 250 ng/mL Dig-3-CME-AMCAP-beta-ala-biotin. After 1 h of incubation the cells were washed with PBS and incubated with the pre-coated anti-Dig magnetic beads. For the enrichment of antigen-reactive B-cells MACS columns (Miltenyi) were used. B-cell sorting and incubation was done as described in Seeber et al. (2014), PLOS One. 2014 Feb. 4; 9 (2). 24 h before performing the ELISA, to identify antigen-reactive clones, 2 µg/mL streptavidin was added to the cell culture supernatants to neutralize free biotin. This was done as a precaution as free biotin in the culture medium or of cellular origin could block the interaction of the antibodies in the supernatant with the screening reagent Dig-3-CME-AMCAP-beta-ala-biotin (Formula III). For the ELISA 96well plates were coated with 5 µg/mL polyclonal goat anti-rabbit-IgG antibody. After a washing step, the plates were blocked with 5% BSA to reduce background signals. The plates were washed again, and 30 µl of the rabbit B-cell cultures were transferred to the 96 well plates and incubated for 1 h at room temperature. After another washing step, 50 ng/ml of the positive screening reagent, Dig-3-CME-AMCAP-beta-ala-biotin, or the negative screening reagent, Dig-3-CME-AMCAP-DADOO-biotin (Formula II), were added to the wells and incubated for 1 h at room temperature. For the detection of antibodies bound to the screening reagents, 3 µg/mL of a POD labeled polyclonal sheep anti-Dig-antibody were added to the plates. After a final washing step, ABTS (Roche) was added as a POD substrate, and positive clones were identified by measuring OD at 405 nm. Results are given in Table 3.

TABLE 3

ELISA results of 4 identified clones producing antibody
characterized by specific binding to the positive
screening reagent according to Formula III but not to
the negative screening reagent according to Formula II.

| clone | Dig-3-CME-AMCAP-beta-ala-biotin (Formula III) | Dig-3-CME-AMCAP-DADOO-biotin (Formula II) |
|---|---|---|
| 5A8 | 1.016 | 0.068 |
| 7D9 | 3.128 | 0.072 |
| 10F7 | 3.171 | 0.097 |
| 29A11 | 3.131 | 0.066 |

Example 7

Binding of Biotin by Monoclonal Antibodies

To demonstrate that the newly generated desired antibodies (including those represented by the clones shown in Table 3) additionally bind to free biotin, a competition ELISA assay was designed and performed.

For this purpose the antibodies were firstly cloned as described in Seeber et al. (2014), PLOS One. 2014 Feb. 4; 9 (2). To generate antibody containing supernatants, HEK cells were transiently transfected with the expression plasmids coding for the relevant heavy and light chains of the anti-biotin antibodies. After 1 week of culture time the concentration of the anti-biotin antibodies in the transient transfections were determined and the concentrations of each of the selected clones were adjusted to 5 µg/ml.

For the ELISA 96well plates were coated with 5 µg/mL polyclonal goat anti-rabbit-IgG antibody. After washing, the plates were blocked with 5% BSA to reduce background signals. The plates were washed again and 30 µl of the antibody supernatants from the transient transfections (5 µg/ml) were transferred into each well of the 96 well plates, and incubated for 1 h at room temperature.

Each of the selected clones was added to 8 different wells in a row to perform a biotin titration.

Following incubation, the plates were washed again 3 times to eliminate the streptavidin/biotin complexes present in the clone supernatants. For the positive control, 50 ng/ml of the positive screening reagent, Dig-3-CME-AMCAP-beta-ala-biotin (Formula III) was added to one of the wells for each antibody, and incubated for 1 h at room temperature.

To test for the binding of free biotin a titration was made. For this purpose, free biotin was added to Dig-3-CME-AMCAP-beta-ala-biotin in increasing concentrations. Biotin was added at concentration of 10 ng/ml, 20 ng/ml, 40 ng/ml, 80 ng/ml, 160 ng/ml, 320 ng/ml and 640 ng/ml to an amount of 50 ng/mL Dig-3-CME-AMCAP-beta-ala-biotin. Afterwards the plates were washed again and for the detection of antibodies bound to Dig-3-CME-AMCAP-beta-ala-biotin, 3 µg/mL of a POD labeled polyclonal sheep anti-Dig-antibody were added to the plates. After a final washing step, ABTS (Roche) was added as a POD substrate and signals were detected by measuring OD(optical density) at 405 nm. Notably, signal reduction was observed was reduced as a result of increasing biotin concentratios in the presence of the screening reagent. This indicates that free-biotinin solution and Dig-3-CME-AMCAP-beta-ala-biotin are competing for binding to the selected antibodies.

Example 8

Counteracting Biotin Interference in an Immunological Assay

The control sample for the Elecsys TSH assay, PreciControl Universal 2 is spiked with rising concentrations of biotin (e.g. 0, 100 and 200 ng/ml final concentration of biotin).

Reagent 2 of the Elecsys TSH sales kit containing the anti TSH detection-antibody is used in a unmodified version (control), and a modified version, additionally containing 300 µg/mL of an monoclonal anti Biotin antibody according to the invention.

The sandwich assay is performed according to the routine assay protocol for the Elecsys TSH assay: Shortly, 50 µL of Sample (PreciControl Universal 2 with or without biotin) are incubated with 60 µL of Reagent 1 of the Elecsys TSH kit containing the biotinylated anti-TSH antibody and 50 µL of Reagent 2 containing the ruthenylated anti-TSH antibody with or without further addition of 300 µg/mL of the monoclonal anti Biotin antibody. After incubation at 37° C. for 9 min, 40 L suspension of streptavidin coated magnetic beads of the Elecsys TSH kit are added, the reaction is incubated for another 9 min and finally the reaction mixture is aspirated into the measuring cell where the microparticles are magnetically captured onto the surface of the electrode. Unbound substances are then removed with ProCell. Application of a voltage to the electrode then induces electrochemiluminescense-based emission of light which is measured by a photomultiplier.

Table 4 shows the signals obtained for the TSH-Reagent variants with or without different anti-biotin scavenger antibody clones:

Using the control reagent, presence of 100 or 200 ng/mL biotin in the sample results in a prominent signal drop to 53% or 16% of the reference signal (sample without biotin).

In contrast to this, in the modified version of the kit containing the biotin binding antibody in reagent R2, the interfering effect of biotin is markedly reduced.

TABLE 4

Signal and signal recovery of sample with different biotin concentrations using reagent without or with different monoclonal anti-biotin antibodie clones

| | | ECL signal [counts] conc. of Biotin in sample [ng/mL] | | | Signal recovery in presence of Biotin conc. of Biotin in sample [ng/mL] | | |
|---|---|---|---|---|---|---|---|
| | | 0 | 100 | 200 | 0 | 100 | 200 |
| | Control w/o anti biotin antibody | 132610 | 70338 | 20947 | 100% | 53% | 16% |
| anti biotin | C | 132542 | 120282 | 102562 | 100% | 91% | 77% |
| | D | 131625 | 126955 | 111922 | 100% | 96% | 85% |

TABLE 4-continued

Signal and signal recovery of sample with different biotin concentrations using reagent without or with different monoclonal anti-biotin antibodie clones

| | | ECL signal [counts] conc. of Biotin in sample [ng/mL] | | | Signal recovery in presence of Biotin conc. of Biotin in sample [ng/mL] | | |
|---|---|---|---|---|---|---|---|
| | | 0 | 100 | 200 | 0 | 100 | 200 |
| anti- | E | 131661 | 127444 | 110127 | 100% | 97% | 84% |
| body | G | 131072 | 127034 | 116162 | 100% | 97% | 89% |
| clone | J | 131626 | 123232 | 106335 | 100% | 94% | 81% |
| | K | 131752 | 127877 | 115760 | 100% | 97% | 88% |

Example 9

Kinetic Antibody Screening

The kinetic screening was performed at 37° C. on a GE Healthcare Biacore 4000 instrument. A Biacore CM5 series S sensor was mounted into the instrument and was hydrodynamically addressed and preconditioned according to the manufacturer's instructions. The system buffer was HBS-EP (10 mM HEPES (pH 7.4), 150 mM NaCl, 1 mM EDTA, 0.05% (w/v) P20). The sample buffer was the system buffer supplemented with 1 mg/ml CMD (Carboxymethyldextran, Fluka).

A rabbit antibody capture system was established on the biosensor. A polyclonal goat anti-rabbit IgG Fc capture antibody GARbFcγ (Code Nr.: 111-005-046, lot #105332, Jackson Immuno Research) was immobilized according to the manufacturer's instructions using NHS/EDC chemistry. 30 µg/ml GARbFcγ in 10 mM sodium acetate buffer (pH 4.5) were preconcentrated to the spots 1, 2, 4 and 5 in the flow cells 1, 2, 3 and 4 and immobilized with 10.000 RU GARbFcγ. The sensor was subsequently saturated with 1 M ethanolamine pH 8.5. The Spots 1 and 5 were used for the interaction measurements and spots 2 and 4 were served as references. Each rabbit antibody clone suspension was diluted 1:2 in sample buffer and was injected at a flow rate of 30 µl/min for 1 min. The rabbit antibody Capture Level (CL) in response units (RU) was monitored.

Since the molecular weight of the 0.9 kDa Dig-Biotin-conjugate is too small for the sensitivity range of the SPR screening instrument, 300 nM Dig-Biotin-conjugate (Dig-3-cme-Amcap-β-Ala-Biotin (BMO No. 15420318)) were preincubated for 2 hours at room temperature with 900 nM<Dig>M-D. G-Fab'. The mAb<Dig>M-D.G-Fab binds to digoxigenin with KD 5 µM affinity. M-D.G-Fab' also binds with picomolar affinity to the digoxigenin moiety in the Dig-Biotin-conjugate and does not interfere with the GARbFcγ capture system. M-D.G-Fab' does not interfere with anti-biotin rabbit clones and free d-biotin. Using the 50 kDa M-D.G-Fab', the 0.9 kDa Dig-Biotin-conjugate was loaded with an additional mass. This results in a highly stable immunocomplex with 50.9 kDa molecular weight, which is optimal for the sensitivity range of the SPR screening instrument. M-D.G-Fab' is monomeric and no analyte avidity effect was generated nor detectable. The preformed Dig-Biotin-conjugate-M-D.G-Fab' complex was singly injected at 30 µl/min for 5 min to monitor the association phase to the respective surface displayed anti-biotin rabbit mAb.

The dissociation of the conjugate from the rabbit clone were monitored for 5 min. After each cycle of kinetic rates determination the rabbit clones were completely washed from the biosensorcapture system by a 1 min injection of 10 mM Glycin pH 2.0 followed by a 2 min injection of 10 mM Glycin pH 2.25 at 20 µl/min.

In a second screening setup, rabbit anti-biotin antibodies, which were sensitive for d-biotin binding interference, were identified. An analyte mixture was prepared by overnight incubation at room temperature, consisting of 300 nM Dig-Biotin-conjugate, 900 nM<Dig>M-D.G-Fab' and 300 nM free d-biotin (d-Biotin, CAS No.: 58-85-5, Catalog No.: 47868, Supelco). The kinetic screening was performed as described before but with this analyte mixture in solution. In another embodiment different Dig-Biotin-conjugate and <Dig>M-D.G-Fab' concentrations were used.

Figure 6A:
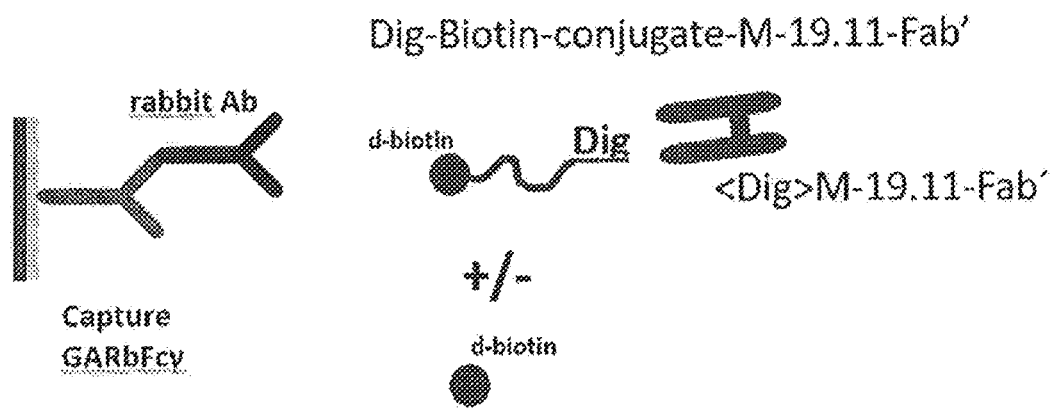
FIG. 6A Kinetic Screening Assay experimental SPR setup. At first, the preformed Dig-Biotin-conjugate-M -19.11-Fab' was used as analyte in solution to monitor the binding for the molecular weight enhanced, conjugated d-biotin. Secondly, the d-biotin was added to the analyte mixture in order to compete with the conjugate binding.
Figure 6B:
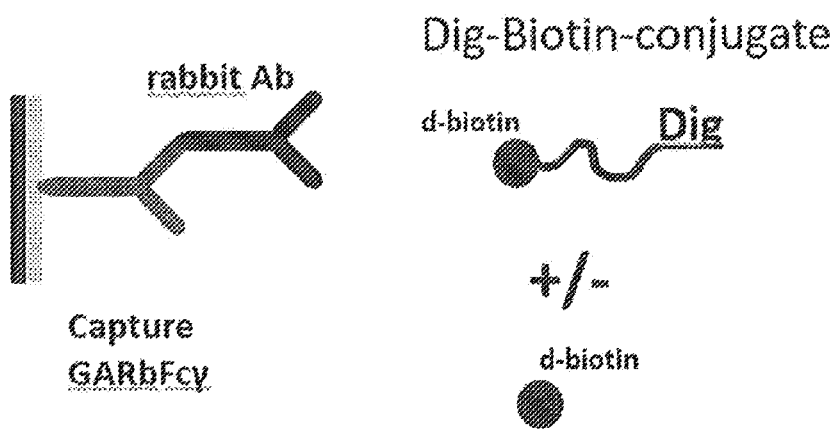
FIG. 6B SPR assay experimental setup. The Dig-Biotin-conjugate interaction was measured in presence and absence of a d-biotin concentration series. In absence of d-biotin, concentration dependent series of the Dig-biotin-conjugate were used to determine the rabbit antibody kinetics versus the Dig-biotin-conjugate. IC50 measurements were performed with a constant concentration of the Dig-biotin-conjugate and increasing concentrations of free d-biotin in the analyte sample mixture.
Figure 6C:
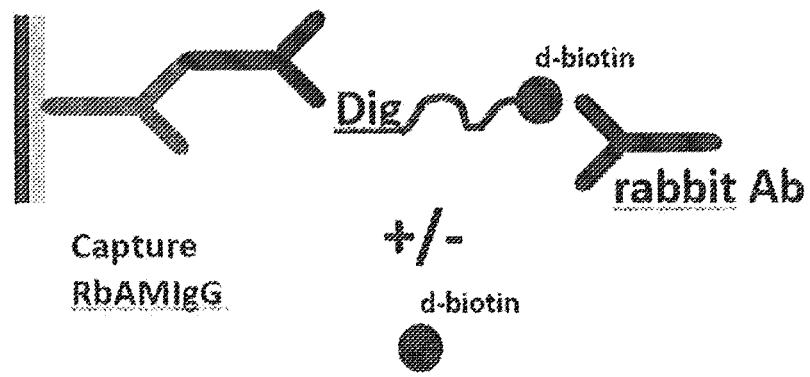
FIG. 6C Alternative SPR assay experimental setup. The Dig-Biotin-conjugate interaction was measured in presence and absence of a d-biotin concentration series. In absence of d-biotin, concentration dependent series of the Dig-biotin-conjugate were used to determine the rabbit antibody kinetics versus the Dig-biotin-conjugate. In this case the Dig-Biotin-conjugate was captured by the surface displayed M-19.11 antibody, whereas the rabbit antibody or fragments thereof were used as concentration dependent analyte in solution. IC50 measurements were performed with a constant concentration of the rabbit antibody and increasing concentrations of free d-biotin in the analyte sample mixture.

FIG. 6 explains the experimental setup for the screening. Several thousand rabbit antibodies were tested by this approach.

The kinetic traces of both analyte single concentration kinetics were monitored by the Biacore 4000 Evaluation Software. Furthermore, the kinetic data was interpreted by report point characterizations and kinetic determinations. Two report points, the recorded signal shortly before the end of the analyte injection, Binding Late (BL) and the signal shortly before the end of the dissociation time, Stability Late (SL), were used to characterize the analyte/antigen binding stability. Furthermore, the dissociation rate constant $k_d$ (1/s) was calculated according to a Langmuir model and the antibody/antigen complex half-life was calculated in minutes according to the Formula ln(2)/(60*kd). The Molar Ratio, the binding stoichiometry was calculated with the formula: MW (antibody)/MW (antigen) *BL (antigen)/CL (antibody).

Finally, the kinetic traces of each anti-biotin rabbit mAb were overlayed in one analysis plot. Mainly by visual inspection of these overlay plots, antibodies were selected, which showed an effective Dig-Biotin-conjugate binding signal reduction in the presence of 300 nM free d-biotin. Effective means, more than 90% Dig-Biotin-conjugate binding signal reduction. In another embodiment antibodies with 80%, 70%, 60%, and 50% signal reduction were selected. Selected antibodies were transferred to detailed IC50 analyses.

Figure 4A:
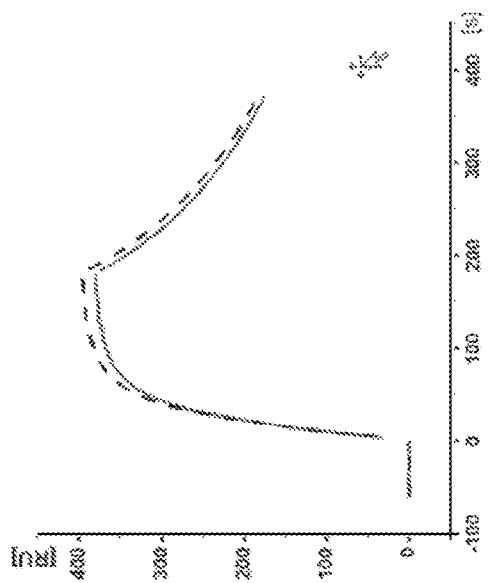
FIG. 4A: complete d-biotin competition.
Figure 4B:
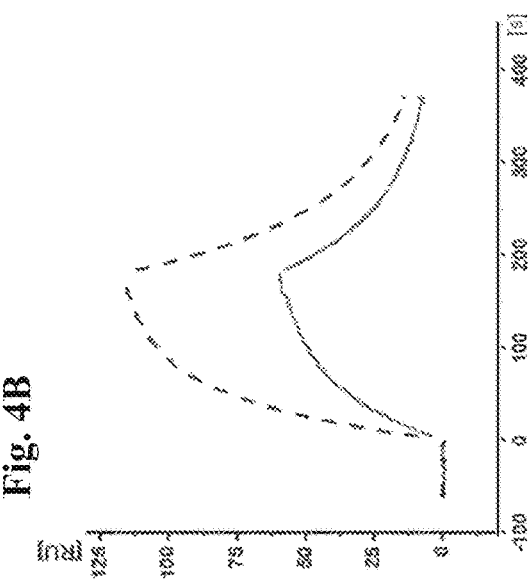
FIG. 4B: Intermediate d-biotin blocking.
Figure 4C:
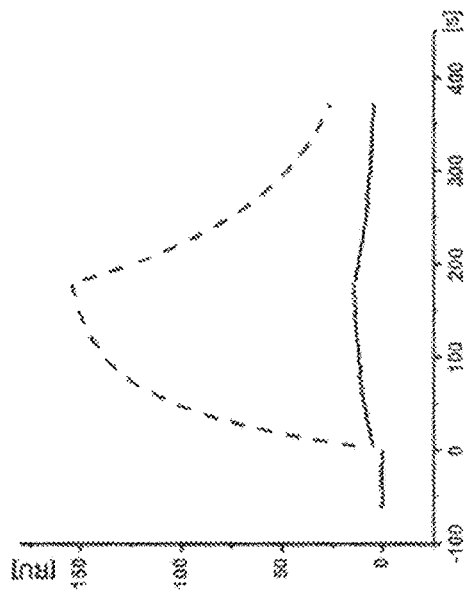
FIG. 4C: No signal interference by d-biotin. Suitable antibody candidates were selected for from the classes in FIG. 4A and FIG. 4B for subsequent detailed investigations.

FIG. 4 exemplarily shows three antibody blocking signatures measured by SPR based kinetic screening. Class A shows full d-biotin blockage of the Dig-Biotin-conjugate binding. Class B features an antibody with just moderate sensitivity for the d-biotin signal interference and Class C is not susceptible to d-biotin.

Detailed SPR Based Functional Analyses

Detailed kinetic investigations were performed at 37° C. on a GE Healthcare T200 instrument. A Biacore CM5 series S sensor was mounted into the instrument and was hydrodynamically addressed and preconditioned according to the manufacturer's instructions. The system buffer was HBS-EP (10 mM HEPES (pH 7.4), 150 mM NaCl, 1 mM EDTA, 0.05% (w/v) P20). The sample buffer was the system buffer supplemented with 1 mg/ml CMD (Carboxymethyldextran, Fluka).

In one embodiment a rabbit antibody capture system was established on the CM5 biosensor. A polyclonal goat anti-rabbit IgG Fc capture antibody GARbFcγ (Code Nr.: 111-005-046, lot #105332, Jackson Immuno Research) was immobilized according to the manufacturer's instructions using NHS/EDC chemistry. 30 µg/ml GARbFcγ in 10 mM sodium acetate buffer (pH 4.5) were preconcentrated to the flow cells 1, 2, 3 and 4 and were immobilized with 10.000 RU GARbFcγ. The sensor was subsequently saturated with 1 M ethanolamine pH 8.5.

Selected rabbit antibody clones from the initial kinetic screening step were diluted in sample buffer at 500 nM each and were captured on the biosensor at a flow rate of 5 µl/min for 2 min followed by a 2 min washing step with 10-fold concentrated HBS-EP system buffer at 60 µl/min. The rabbit antibody Capture Level (CL) in response units (RU) was monitored. The higher sensitivity of the T200 instrument circumvented the additional molecular mass load by <Dig>M-D.G-Fab'. A series of analytes was injected at 60 µl/min for 5 min association phase and the dissociation phase was monitored for 5 min. First, the Dig-Biotin-conjugate analyte was injected at 300 nM omitting d-biotin in solution. Then, increasing d biotin concentrations of 4 nM, 8 nM, 15 nM, 30 nM, 90 nM and 270 nM were added to the Dig-Biotin-conjugate mixture. Sensorgram overlay plots were produced to analyze the Dig-Biotin-conjugate binding signal suppression by the presence of increasing d-biotin concentrations. The Binding Late report points from the signal plateau of the analyte association phase were plotted over the increasing d-biotin concentrations and the d-biotin IC50 values were determined using the point-to-point mode in Biaevaluation software. Furthermore, the sensorgram overlay plots were visually investigated for the competing performance of d-biotin and a % signal suppression was estimated. In another embodiment the % signal blocking was calculated by comparison of the 0 nM d-biotin and the 270 nM d-biotin sample injections.

FIG. 6 shows the SPR experimental setup of the IC50 measurements. FIG. 6B shows the preferred embodiment.

Figure 5:
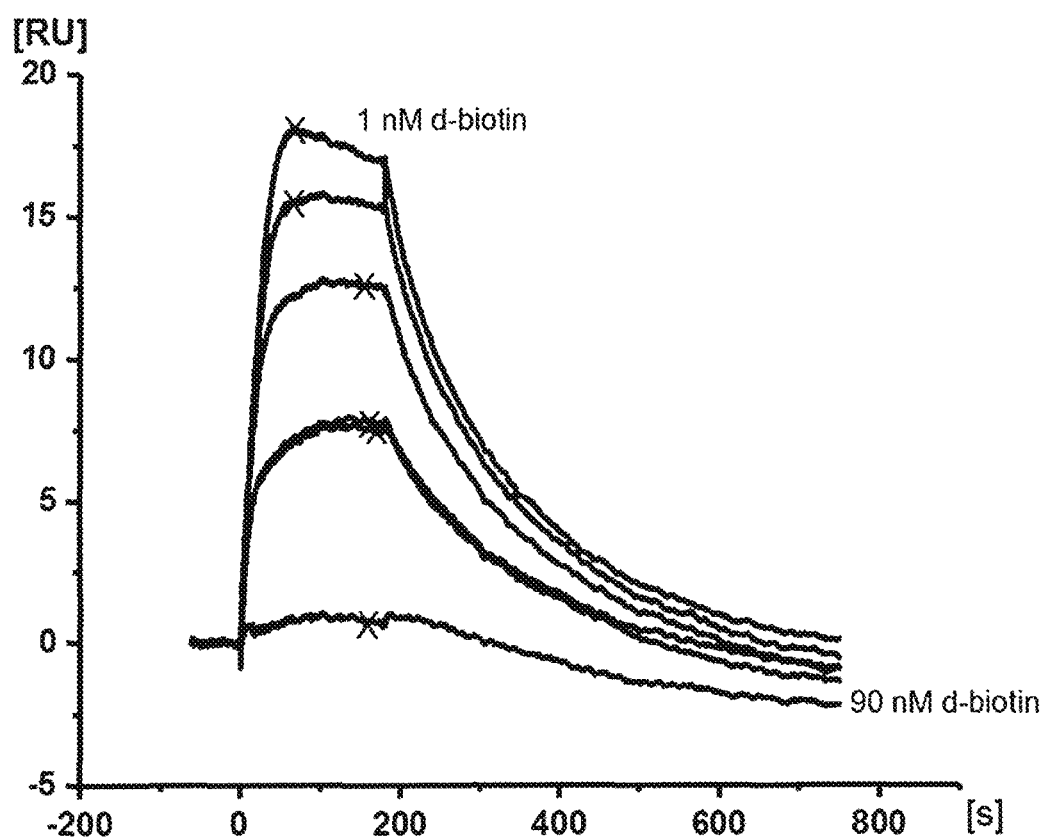
FIG. 5 Exemplary SPR Sensorgram overlay plot of the lead antibody candidate clone G SPR IC50 measurement. 270 nM Dig-Biotin-conjugate was mixed with free d-biotin concentrations at 270 nM (not shown), 90 nM, 30 nM (twice), 10 nM, 3.3 nM and 1 nM. The mixture containing 90 nM free d-biotin concentration produced the lowest response signal and with 1 nM free d-biotin produced the highest response signal (labelled). X indicates the positions of the report points, which were used for the IC50 calculation.

FIG. 5 exemplary shows a result of this competition assay. Shown is the antibody lead candidate G. The higher the free d-biotin concentration in the sample, the lower is the Dig-Biotin-conjugate binding signal and thus it was estimated the antibody's susceptibility for d-biotin binding. The IC50 determination of the clone G was IC50=30 nM d-biotin.

In another embodiment the kinetic parameters ka [1/Ms], kd [1/s], t1/2 diss [min], KD [M] and the binding stoichiometry (Molar Ratio) of the Dig-Biotin-conjugate binding antibody were determined.

The 37° C. kinetics of clone G were determined with ka=5.8*10E5 1/Ms, kd=2.1*10E-2 (1/s), t1/2 diss=1 min, MR=1.2. The affinity for the Dig-Biotin-conjugate was KD=36 nM.

The 37° C. kinetics of clone A were determined with ka=1.0*10E6 1/Ms, kd=3.0*10E-4 (1/s), t1/2 diss=39 min, MR=1.5. The affinity for the Dig-Biotin-conjugate was KD=0.3 nM.

In one embodiment, the T200 instrument assay setup was as described above. The Dig-Biotin-conjugate was injected in a concentration serie at 0 nM, 4 nM, 8 nM, 15 nM, 30 nM, 90 nM and 270 nM. Kinetic parameters were determined using the Biacore evaluation software.

In another embodiment the kinetic parameters ka [1/Ms], kd [1/s], t1/2 diss [min], KD [M] and the binding stoichiometry (Molar Ratio) of the Dig-Biotin-conjugate antibody binding were determined by an alternative sensor surface setup. In one embodiment a murine antibody capture system was established on the CM5 biosensor. A polyclonal rabbit anti-mouse IgG capture antibody (RbAMIgG (rabbit anti mouse IgG), pAb<M-IgG>Rb-IgG (IS), BR-1008-38, 2017-08, GE Healthcare) was immobilized according to the manufacturer's instructions using NHS/EDC chemistry. 30 µg/ml GARbFcγ in 10 mM sodium acetate buffer (pH 5.0) were preconcentrated to the flow cells 1, 2, 3 and 4 and were immobilized with 10.000 RU. The sensor was subsequently saturated with 1 M ethanolamine pH 8.5.

Approximately 300 RU of 30 nM mAb<Dig>M$^{-19/11}$-IgG (Q) (Roche, 28 Jan. 1999, entrance 19.5.2017, Id. 2157861) were captured at 10 µl/min for 1 min. The Dig-Biotin-conjugate was injected at 150 nM for 2 min at 30 µl/min to be stably captured by M$^{-19/11}$-IgG.

FIG. 6 is describing the assay setup. This assay was preferably used for the kinetic determination of recombinantely expressed rabbit anti-biotin Fab' fragments.

Then anti-biotin rabbit antibodies or fragments thereof were injected in concentration dependent series as described above in order to determine binding kinetics.

Example 10

ITC Experiments

The goal of the ITC experiments was to directly determine the affinity of the selected antibodies to free biotin in solution and the thermodynamic parameters and stoichiometry of binding reaction.

All ITC experiments were conducted on a VP-ITC microcalorimeter (Malvern Instruments). The experiments were performed at 25° C. in phosphate buffer (25 mM potassium phosphate pH 7.4, 150 mM potassium chloride). Protein concentrations were 750 µg/ml for the monoclonal antibodies resulting in a molar concentration of 10 µM for the paratopes. Biotin concentrations were 100 µM. The titrations were carried out with a stirring speed of 310 rpm and 200 s time intervals between 10 µl injections. The first injection for each sample was excluded from the data fitting. The experimental data were fitted to a theoretical curve using the NanoAnalyze Data Analysis software package (Version 3.6.0) to afford values for $K_d$ (dissociation constant in M), n (stoichiometry of binding) and ΔH (the change in enthalpy in kcal/mol). The thermodynamic parameters (ΔG and ΔS) were calculated from $K_d$ and ΔH using the equation:

$$\Delta G = RT\ln(K_d) = \Delta H - T\Delta S$$

where R is the universal gas constant, T the temperature and ΔG, ΔH and ΔS are the changes in Gibbs free energy, enthalpy and entropy.

TABLE 5

| monoclonal antibody | $K_d$ nM | n | ΔH kcal/mol | ΔG kcal/mol | −TΔS kcal/mol |
|---|---|---|---|---|---|
| N | 5.5 | 1.09 | −13 | −11.3 | 2 |
| M | 10.5 | 0.92 | −21 | −10.9 | 10 |
| L | 4.4 | 1.07 | −17 | −11.4 | 5 |
| J | 1.6 | 1.03 | −20 | −12.0 | 8 |
| K | 0.7 | 1.00 | −16 | −12.5 | 3 |
| G | 1.0 | 1.04 | −15 | −12.3 | 3 |
| F | 1.0 | 1.00 | −20 | −12.3 | 8 |

Example 11

Purification of Fab Fragments from Prokaryotic Cell Fermentation

The expressed polypeptides of the present invention are secreted into and recovered from the periplasm of the host cells. The cells may be harvested by centrifugation or filtration. After resuspension of the biomass in an appropriate buffer with a pH between 2.0 and 8.0 or using the complete fermentation broth the cells are disrupted by physical, chemical or enzymatic methods. Once cells are disrupted, cell debris or whole cells may be removed by centrifugation or filtration. The purification of the polypeptides may involve several precipitation steps and fractionation on cation, anion exchange chromatography, hydrophobic interaction, mixed mode, affinity or gel filtration chromatography. For the removal of trace amounts of bound biotin a treatment of the polypeptide solution with a binding agent e.g. streptavidin may be necessary. For the final formulation of the polypeptide dialysis, ultrafiltration or ultradialysis steps may be conducted. The polypeptide may be stored as liquid, a frozen liquid or as a spray dried or freeze dried solid.

The invention claimed is:

1. An immunogen according to Formula I:

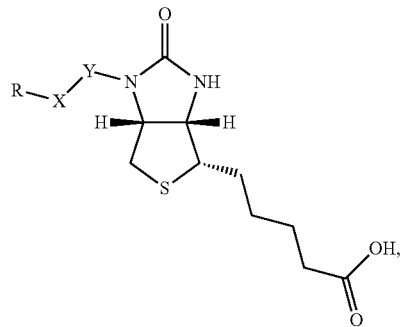

(Formula I)

wherein:
R is Z-L,
L-X-Y together are suberyl-beta-alanyl, and
Z is a polypeptide of at least 30 amino acids.

2. An immunogen, wherein said immunogen is KLH-suberyl-beta-alanyl-biotin.

* * * * *